(12) United States Patent
Bauer

(10) Patent No.: US 10,076,297 B2
(45) Date of Patent: Sep. 18, 2018

(54) PHASE CONTRAST X-RAY TOMOGRAPHY DEVICE

(71) Applicant: ARP ANGEWANDTE RADIOLOGISCHE PHYSIK UG (HAFTUNGSBESCHRANKT), Eberdingen-Nussdorf (DE)

(72) Inventor: Walter Bauer, Eberdingen-Nussdorf (DE)

(73) Assignee: ARP ANGEWANDTE RADIOLOGISCHE PHYSIK UG (HAFTUNGSBESCHRANKT), Eberdingen-Nussdorf (DE)

( * ) Notice: Subject to any disclaimer, the term of this patent is extended or adjusted under 35 U.S.C. 154(b) by 474 days.

(21) Appl. No.: 14/387,786

(22) PCT Filed: Mar. 22, 2013

(86) PCT No.: PCT/EP2013/000873
§ 371 (c)(1),
(2) Date: Feb. 23, 2015

(87) PCT Pub. No.: WO2013/143672
PCT Pub. Date: Oct. 3, 2013

(65) Prior Publication Data
US 2015/0279496 A1    Oct. 1, 2015

(30) Foreign Application Priority Data
Mar. 25, 2012   (DE) .................. 10 2012 005 767

(51) Int. Cl.
*A61B 6/00*    (2006.01)
*A61B 6/03*    (2006.01)
(Continued)

(52) U.S. Cl.
CPC .............. *A61B 6/484* (2013.01); *A61B 6/032* (2013.01); *A61B 6/035* (2013.01); *A61B 6/4021* (2013.01);
(Continued)

(58) Field of Classification Search
CPC ....... A61B 6/032; A61B 6/035; A61B 6/4021; A61B 6/4028; A61B 6/4035;
(Continued)

(56) References Cited

U.S. PATENT DOCUMENTS 4,075,489 A * 2/1978 Neal ...................... A61B 6/032
378/10
4,122,346 A * 10/1978 Enge ...................... A61B 6/032
250/396 ML
(Continued)

FOREIGN PATENT DOCUMENTS

DE   102006046034   8/2007
DE   102007036038   2/2009
WO   WO2009115966   9/2009

OTHER PUBLICATIONS

International Search Report cited in PCT/EP2013/000873, dated Jun. 4, 2013.

*Primary Examiner* — Allen C. Ho
(74) *Attorney, Agent, or Firm* — Lempia Summerfield Katz LLC

(57) ABSTRACT

The invention relates to a phase contrast x-ray tomography device, comprising an electron gun (44) having a downstream deflector coil (52). The x-ray beam (56) is guided by the deflector coil (54) on a circular path over a target (58), which is marginally tilted towards a plane positioned vertically on the device axis. The x-ray beam (62) generated at
(Continued)

focal spot F of the electron beam (56) crosses an object (70) and arrives at a detector line (68) via a phase grating (64) and an amplitude grating (66).

33 Claims, 18 Drawing Sheets

(51) Int. Cl.
G01N 23/046 (2018.01)
G01N 23/20 (2018.01)
G21K 1/06 (2006.01)
H05G 1/30 (2006.01)

(52) U.S. Cl.
CPC .......... A61B 6/4028 (2013.01); A61B 6/4035 (2013.01); A61B 6/4085 (2013.01); A61B 6/4233 (2013.01); A61B 6/4435 (2013.01); A61B 6/4441 (2013.01); G01N 23/046 (2013.01); G01N 23/20075 (2013.01); G21K 1/067 (2013.01); H05G 1/30 (2013.01); A61B 6/548 (2013.01); G21K 2201/067 (2013.01); G21K 2207/005 (2013.01)

(58) Field of Classification Search
CPC ... A61B 6/4085; A61B 6/4233; A61B 6/4435; A61B 6/4441; A61B 6/484
USPC .......... 378/10, 36, 38–40, 62, 98.6
See application file for complete search history.

(56) References Cited

U.S. PATENT DOCUMENTS

| | | | | |
|---|---|---|---|---|
| 4,130,759 A | * | 12/1978 | Haimson | A61B 6/032 378/10 |
| 4,135,095 A | * | 1/1979 | Watanabe | A61B 6/032 378/10 |
| 4,219,733 A | * | 8/1980 | Tschunt | A61B 6/032 378/10 |
| 4,352,021 A | * | 9/1982 | Boyd | A61B 6/032 378/10 |
| 4,392,235 A | * | 7/1983 | Houston | A61B 6/032 378/10 |
| 4,521,900 A | * | 6/1985 | Rand | H01J 35/00 250/396 R |
| 4,521,901 A | | 6/1985 | Rand | |
| 4,531,226 A | * | 7/1985 | Peschmann | A61B 6/032 313/237 |
| 4,535,243 A | * | 8/1985 | Peschmann | A61B 6/032 250/363.02 |
| 4,573,179 A | * | 2/1986 | Rutt | A61B 6/032 378/10 |
| 4,610,021 A | * | 9/1986 | Peschmann | A61B 6/032 378/150 |
| 4,618,970 A | * | 10/1986 | Rand | A61B 6/032 378/10 |
| 4,625,150 A | * | 11/1986 | Rand | H01J 3/40 313/424 |
| 4,644,168 A | * | 2/1987 | Rand | A61B 6/032 250/396 ML |
| 4,669,102 A | * | 5/1987 | Puumalainen | A61B 6/032 378/10 |
| 4,672,649 A | * | 6/1987 | Rutt | A61B 6/032 348/E13.014 |
| 4,736,396 A | * | 4/1988 | Boyd | A61B 6/025 378/10 |
| 4,914,681 A | * | 4/1990 | Klingenbeck | A61B 6/032 378/10 |
| 4,944,448 A | * | 7/1990 | Peschmann | A61B 6/032 228/173.2 |
| 4,962,513 A | * | 10/1990 | Schwierz | A61B 6/032 378/12 |
| 5,164,972 A | * | 11/1992 | Krumme | A61B 6/032 370/534 |
| 5,172,401 A | * | 12/1992 | Asari | H01J 35/14 378/10 |
| 5,193,105 A | * | 3/1993 | Rand | H01J 35/04 250/396 ML |
| 5,212,737 A | * | 5/1993 | Ackelsberg | A61B 6/032 378/21 |
| 5,224,137 A | * | 6/1993 | Plomgren | A61B 6/032 378/10 |
| 5,247,556 A | * | 9/1993 | Eckert | A61B 6/032 378/21 |
| 5,377,249 A | * | 12/1994 | Wiesent | A61B 6/032 378/10 |
| 5,386,445 A | * | 1/1995 | Rand | A61B 6/032 378/10 |
| 5,406,479 A | * | 4/1995 | Harman | G01N 23/046 378/7 |
| 5,442,673 A | * | 8/1995 | Rand | A61B 6/4028 378/10 |
| 5,490,193 A | * | 2/1996 | Kuroda | A61B 6/032 378/10 |
| 5,491,734 A | * | 2/1996 | Boyd | A61B 6/032 378/10 |
| 5,504,791 A | * | 4/1996 | Hell | A61B 6/032 378/10 |
| 5,528,658 A | * | 6/1996 | Hell | H01J 35/30 378/121 |
| 5,548,630 A | * | 8/1996 | Hell | A61B 6/032 378/121 |
| 5,633,906 A | * | 5/1997 | Hell | A61B 6/032 378/10 |
| 5,654,995 A | * | 8/1997 | Flohr | A61B 6/4028 378/10 |
| 5,719,914 A | * | 2/1998 | Rand | G01N 23/046 378/10 |
| 5,995,586 A | * | 11/1999 | Jahnke | H05G 2/00 378/10 |
| 6,130,929 A | * | 10/2000 | Saha | G06T 11/006 378/10 |
| 6,160,869 A | * | 12/2000 | Zapalac | H01J 35/30 378/10 |
| 6,208,711 B1 | * | 3/2001 | Rand | G21K 1/08 378/131 |
| 6,628,745 B1 | * | 9/2003 | Annis | A61B 6/032 378/10 |
| 6,687,332 B2 | * | 2/2004 | Smyth | A61B 6/4028 378/10 |
| 6,735,271 B1 | * | 5/2004 | Rand | A61B 6/032 378/15 |
| 6,765,983 B2 | * | 7/2004 | Yan | A61B 6/032 378/8 |
| 6,789,943 B2 | * | 9/2004 | Zapalac | A61B 6/032 378/18 |
| 6,792,077 B2 | * | 9/2004 | Rand | A61B 6/032 378/147 |
| 6,842,499 B2 | * | 1/2005 | Zapalac | A61B 6/032 378/12 |
| 6,934,357 B2 | * | 8/2005 | Boyd | A61B 6/032 378/62 |
| 6,993,111 B1 | * | 1/2006 | Annis | G01N 23/04 378/57 |
| 7,023,950 B1 | * | 4/2006 | Annis | G01N 23/046 378/119 |
| 7,033,076 B2 | * | 4/2006 | Sengupta | A61B 6/032 378/137 |
| 7,281,850 B2 | * | 10/2007 | Varadharajan | A61B 6/583 378/10 |
| 7,340,029 B2 | * | 3/2008 | Popescu | A61B 6/032 378/10 |
| 7,428,297 B2 | * | 9/2008 | Eilbert | G01N 23/2252 378/10 |
| 7,433,444 B2 | * | 10/2008 | Baumann | A61B 6/032 378/145 |
| 7,440,542 B2 | * | 10/2008 | Baumann | A61B 6/484 378/44 |

(56) References Cited

U.S. PATENT DOCUMENTS

| | | | |
|---|---|---|---|
| 7,447,536 B2 * | 11/2008 | Hill | A61B 6/032 378/138 |
| 7,453,981 B2 * | 11/2008 | Baumann | A61B 6/484 378/21 |
| 7,486,770 B2 * | 2/2009 | Baumann | A61B 6/032 378/145 |
| 7,492,871 B2 * | 2/2009 | Popescu | A61B 6/00 378/145 |
| 7,522,708 B2 * | 4/2009 | Heismann | A61B 6/00 378/145 |
| 7,532,704 B2 | 5/2009 | Hempel | |
| 7,535,986 B2 * | 5/2009 | Hempel | A61B 5/02007 378/4 |
| 7,564,941 B2 * | 7/2009 | Baumann | A61B 6/484 378/146 |
| 7,580,500 B2 * | 8/2009 | Forster | A61B 6/032 378/10 |
| 7,634,045 B2 | 12/2009 | Popescu | |
| 7,639,786 B2 * | 12/2009 | Baumann | A61B 6/484 378/145 |
| 7,646,843 B2 * | 1/2010 | Popescu | A61B 6/032 356/521 |
| 7,660,391 B2 * | 2/2010 | Oreper | A61B 6/032 378/123 |
| 7,688,937 B2 * | 3/2010 | Schomberg | A61B 6/032 378/10 |
| 7,817,777 B2 * | 10/2010 | Baumann | A61B 6/00 378/36 |
| 7,839,967 B2 * | 11/2010 | Grass | A61B 6/032 378/10 |
| 7,872,241 B2 * | 1/2011 | Rand | H01J 35/08 250/396 ML |
| 7,876,879 B2 * | 1/2011 | Morton | G01T 1/2985 378/57 |
| 7,889,838 B2 * | 2/2011 | David | A61B 6/4233 378/36 |
| 7,945,018 B2 * | 5/2011 | Heismann | A61B 6/032 378/145 |
| 7,949,101 B2 * | 5/2011 | Morton | G01N 23/06 378/124 |
| 7,983,381 B2 * | 7/2011 | David | A61B 6/032 378/4 |
| 7,983,384 B2 * | 7/2011 | Hampel | A61B 6/032 378/10 |
| 8,130,899 B2 * | 3/2012 | Hampel | A61B 6/032 378/10 |
| 8,139,711 B2 * | 3/2012 | Takahashi | A61B 6/00 356/457 |
| 8,223,919 B2 * | 7/2012 | Morton | G01N 23/046 378/57 |
| 8,270,565 B2 * | 9/2012 | Oreper | G03B 42/02 378/19 |
| 8,401,143 B2 * | 3/2013 | Hampel | A61B 6/032 378/10 |
| 8,451,974 B2 * | 5/2013 | Morton | G01N 23/04 378/10 |
| 8,530,849 B2 * | 9/2013 | Boyd | A61N 5/10 250/370.09 |
| 8,565,371 B2 | 10/2013 | Bredno | |
| 8,913,714 B2 * | 12/2014 | Michel | G01N 23/20075 250/370.09 |
| 9,084,528 B2 * | 7/2015 | Geller | A61B 6/00 |
| 9,155,510 B2 * | 10/2015 | Chen | G01N 23/046 |
| 9,269,469 B2 * | 2/2016 | Suft | G21K 1/06 |
| 9,412,554 B2 * | 8/2016 | Behling | G21K 1/02 |
| 9,453,803 B2 * | 9/2016 | Radicke | H01J 35/14 |
| 9,460,823 B2 * | 10/2016 | Song | H05K 7/2039 |
| 9,532,760 B2 * | 1/2017 | Anton | G21K 1/065 |
| 9,763,634 B2 * | 9/2017 | Preusche | A61B 6/4035 |
| 2003/0235271 A1 | 12/2003 | Rand | |
| 2007/0183559 A1 | 8/2007 | Hempel | |
| 2009/0034678 A1 | 2/2009 | Popescu | |
| 2009/0154640 A1 | 6/2009 | Baumann et al. | |
| 2010/0061508 A1 | 3/2010 | Takahashi | |
| 2011/0261924 A1 | 10/2011 | Bredno | |

* cited by examiner

PHASE CONTRAST X-RAY TOMOGRAPHY DEVICE

The invention relates to a phase contrast x-ray tomography device.

Objects can be detected in radiography both by the fact that the incident radiation in the object is weakened, or else by the fact that the incident radiation in the object has a different velocity of propagation than outside the same. The above also applies to the detection of structures within an object.

Changes in the velocity of propagation lead to changes in the phase position of the wavefronts behind the object. Typical methods for detecting the change of phase positions consist in using the light which has passed through the object to generate interference figures and measuring their brightness distribution with suitable detectors.

Such detectors are today, in particular, row detectors which have a large number of detection pixels following one another at close spacing regularly in the detector longitudinal direction. The output signals of such detectors can be shaped and evaluated by applying known techniques.

If, instead of row detectors, strip detectors are used, which have detector elements following one another regularly at a small spacing in a direction perpendicular to the detector longitudinal direction, the number of which however is less than in the detector longitudinal direction, the interference figures can also be evaluated in a second direction, with the result that the quality of the image can be improved or the time required for capturing the image can be reduced. For simplification, unless otherwise stated, row detectors are to be understood here also as strip detectors, in order to avoid duplicate mentions.

The possibility, just mentioned, of detecting structures of an object by utilising the fact that light has a different velocity of light in different regions of matter is also called a phase contrast method, since a high-contrast representation of the object is derived from phase differences in the position of the wavefronts.

Phase contrast methods are of great interest in particular where materials absorb light only a little, i.e. are largely transparent to the light used.

Such conditions exist, in particular, in the field of x-ray radiograms, since x-rays, as are commonly used in medical diagnostics and in material testing, are absorbed only a little by materials which occur in organic tissues. As is known, the absorption of x-rays in matter depends to a great extent on the atomic number of the atoms found therein. Organic matter is, however, composed predominantly of hydrogen atoms, carbon atoms, nitrogen atoms and oxygen atoms, which are all elements having a low atomic number.

In DE 10 2006 046 034 A1, also published as U.S. Pat. No. 7,532,704 B2, there has already been described a phase contrast x-ray tomography device which operates according to the principle described at the outset. In this known x-ray tomography device, the interference pattern is generated by two x-ray gratings arranged at different spacing in alignment in front of a linear detector. Specifically, DE 10 2006 046 034 A1 is concerned with providing a phase contrast x-ray tomography device which can be used at the same time also for conventional radiograms which are based on the different absorption of the x-rays in different regions of the examination object.

In the known x-ray tomography device, an x-ray source and a phase measuring device are arranged on a circular guide (gantry) diametrically opposite one another. They rotate in a rigid relative position about the axis of the gantry. This axis is also referred to below simply as the device axis.

Upon rotation of x-ray source and phase measuring device, a body, e.g. a patient, to be examined which is arranged on the device axis is irradiated from different directions. The x-ray beam used for the irradiation has only small dimensions in the direction of the device axis, i.e. has the shape of a very flat fan. Upon a rotation of x-ray source and phase measuring device, a layer of the object to be examined is thus acquired. Owing to the fact that a relative movement between the gantry and the object to be examined is produced in the axial direction, a large number of closely adjacent sections through the object can be created.

On account of the mechanical inertia of the rotating device parts, the temporal resolution of the known tomograph is low. Moving structures such e.g. the pulsating heart muscle thus cannot be resolved.

In phase contrast x-ray computer tomography, x-ray gratings with very small grating constants must be used in the phase measuring device. These x-ray gratings must be positioned extremely accurately and moreover also displaced very precisely by small distances in order to produce specific small changes in the interference patterns which are important for the evaluation of the interference patterns. Consequently, the known tomography device must have a very stable structure, in order to reliably exclude vibration-induced or distortion-induced changes in the interference pattern. Since the gantry has to surround an examination region which is typically significantly larger than the dimensions of a human body, such tomography devices are also very bulky.

Also known are x-ray tomography devices in which a rotating x-ray fan is generated by focusing an electron beam, rotated (=moved on a circular path) by a deflecting coil and provided by an electron gun of the device, onto a ring-shaped target arranged stationarily in the gantry. Such a tomography device is described in U.S. Pat. No. 4,521,901. Here, there are thus no heavy and sluggish rotating device parts, and organs which are moving can also be examined with such a device.

This device, however, operates in absorption and thus produces conventional x-ray tomograms.

An improved phase contrast x-ray tomography device is to be provided by the present invention.

This object is achieved according to the invention by a phase contrast x-ray tomography device having the features disclosed herein.

The phase contrast x-ray tomography device according to the invention can be constructed very largely without moving mechanical parts. This is because the x-ray light source, with the electron beam moving on a path over a target, allows a rotating x-ray beam to be generated without mechanically rotated components. In particular, source, grating and detector are mechanically stationary, thereby ensuring that the phase measuring device ensures high stability and high constancy of its working behaviour.

Advantageous developments of the invention are specified in the claims, written description, and drawings.

The development of the invention according to an embodiment is advantageous with regard to an effect modulation and good signal conditioning in the signal channels connected to the detector row.

In a tomography device according to another embodiment, the x-ray fan always stays for a short period of time in the same position relative to the object and is then advanced by one increment at a time. This is advantageous with regard to low-noise and high-contrast images.

In a tomography device according to another embodiment, the focal point of the electron beam on the target and hence the origin of the x-ray beam can be varied such that the width of the x-ray beam fan can be adjusted. In one embodiment of the tomography device, the radial position of the electron beam can be varied, preferably in dependence on a size of a region to be irradiated.

In a tomography device according to another embodiment, the focus of the electron beam and hence the point of origin of the x-ray beam can be moved on a circle. It is thus possible to subject an object to x-ray light from different directions substantially perpendicular to an object axis. If the target here has the shape of a truncated cone, the radial displacement of the focal point of the electron beam is accompanied at the same time by an axial displacement of the same. In this way, the position of the x-ray beam can also be varied in the axial direction. As a result, an axial movement of the x-ray-light diffraction structures which may be necessary for phase measurement to be dispensed with.

The preferred development here, in which the opening angle of the target cone is chosen such that it is suitable for a Talbot interferometer of the phase measuring device, is advantageous with regard to low radiation dose and to the spatial coherence necessary for forming high-contrast interference stripes.

In a tomography device according to another embodiment, a part of the x-ray spectrum is retained by a filter wall before the x-ray beam impinges on the object to be examined. This is advantageous with regard to x-ray generation with high power density and to high-contrast interference patterns.

Another embodiment is advantageous with regard to an effective x-ray radiation generation with at the same time a low weight of the device. The functional layer here can be a very thin layer made of functional material, the thickness of which is preferably adapted to the anode voltage and the penetration depth of the electron beam and further preferably is less than 20 µm, preferably less than 10 µm, and which is preferably produced by vapor deposition or sputtering. This is advantageous with regard to good x-ray generation on the one hand and good heat dissipation on the other hand.

Normally the phase measuring device used here works only in a narrow wavelength range of the x-ray light. Therefore, the development of another embodiment is advantageous, according to which the phase measuring device and the functional material used for the target are matched to one another such that at feast of the material-specific, sharp lines of the x-ray spectrum of the x-ray light source is at a wavelength for which the phase measuring device is optimized. The x-ray properties of the object to be examined are also important when selecting the functional material.

A tomography device according to another embodiment is particularly well suited for an examination of an object from all sides. The circular shape or polygonal shape here is advantageous, but not absolutely necessary, with regard to the production of complete data and the ensuring of largely identical examination conditions in the circumferential direction.

In a tomography device according to another embodiment, interference image generated in the phase measuring device can be evaluated in two mutually perpendicular directions. This enables the phase measurement in a resolved image pixel with only one exposure without including too many detector pixels in the circumferential direction. The imaging speed can thus be increased without deterioration of the resolution in the circumferential direction.

The development of another embodiment makes it possible to use in the tomography device also an x-ray light source which has ordinary focus sizes, i.e. originally generates x-ray light which is not sufficiently spatially coherent. Owing to the x-ray grating arranged behind the x-ray light source, an approximately coherent portion is removed from the x-ray light generated by the x-ray light source and is then used for the phase contrast examination.

The development of another embodiment enables the dual use of the x-ray grating both as a coherence grating and as a phase measuring grating. For, in an x-ray grating at least sectionally, preferably completely, surrounding the examination region, the x-ray light emitted by the focal spot can pass through the x-ray grating firstly substantially radially from the outside inwards, in order to generate x-ray light sufficiently coherent for the phase contrast measurement. After passing through the examination region, the x-ray light passes through the x-ray grating on the diametrically opposite side of the examination region in the opposite direction, i.e. radially from the inside outwards, so that the x-ray grating serves as an x-ray light diffraction structure for measuring the phase position. This allows the use of only one x-ray grating if the detector resolution is sufficient to detect the interference patterns resulting on the measurement of the phase position. Otherwise, a further x-ray-light diffraction structure must be provided.

The developments of another embodiment are advantageous with regard to the formation of a high-contrast interference pattern in the phase measuring device.

The development of another embodiment is advantageous therein with regard to good sensitivity and contrast resolution of the tomography device.

In a tomography device according to another embodiment, long-wave regions of the spectrum of the x-ray light source could adversely affect the phase contrast image as a background are removed.

The development of another embodiment is also advantageous with regard to the examination of object in different radial directions.

The development of another embodiment allows the target, the first interference device and optionally also a filter wall to be combined in a single component. In addition, an irradiation lying exactly in the target plane and without axial displacement is thereby also possible, with the result that a higher image quality can be achieved.

The development of another embodiment likewise allows an irradiation lying exactly in the target plane, wherein all the materials penetrated on the way to the detector can be optimized in their absorption and filtering direction in the object direction and opposite the object direction.

The development of another embodiment allows the interference patterns to be varied, with previously known small changes in the relative positions of light source, diffraction structures and detector row, and the phase position of the x-ray light in the phase measuring device to be determined from the small changes of the interference stripes, with known relative movements. This makes it possible, in contrast to the prior art, to determine the phase position of the x-ray light temporally successively and therefore with an exact spatial resolution corresponding to the size of the detector pixels.

Another embodiment of the present disclosure specifies concrete means of how the change of the interference conditions is precisely and reproducibly changed and thus the phase measurement can now be determined temporally successively. Spatially resolved exactly to the phase measurement resolved exactly to a pixel size, instead of performing the phase measurement with a plurality of detector pixels simultaneously.

The development according to another embodiment is advantageous with regard to guiding the x-ray beam exactly horizontally in relation to the device axis. In an x-ray tomography device according to this embodiment, at least parts of the phase measuring device are also easily accessible, which facilitates their adjustment.

Through the development of another embodiment, the x-ray beam has a small dimension in the axial direction of the device. It is thus possible to examine correspondingly thin layers of the examined object (workpiece, patient), As a result, the dose load of a patient can also be reduced. Furthermore, in this way the required grating and detector extent in the axial direction can be markedly reduced, thereby reducing the costs for production.

In a tomography device according to another embodiment, the x-ray fan is also limited in the circumferential direction.

Such a limitation is obtained according to another embodiment in a mechanically particularly simple manner, since the screens do not need to be rotating. In connection with this development, the electron beam and hence the x-ray beam generated by the latter is then advanced incrementally in such a way that, in each cycle, the next window bounded by the screens following one another in the circumferential direction is reached.

In a tomography device according to another embodiment, use is made of the incremental advancing of the electron beam to position the x-ray fan, generated by the electron beam, successively in the different windows of the screen body.

With the development of another embodiment, it is possible to pivot the axis of the x-ray fan out of an exactly radial direction. This embodiment makes it possible to irradiate a partial region of an object.

Furthermore, according to another embodiment a screen rotating synchronously with the x-ray beam can be used to laterally limit the x-ray beam in the fan plane. The use of rotating screens here has the advantage that the said dimension of the x-ray beam can be varied in a greater range, depending on the application.

The development of another embodiment allows a detector row or a detector strip to be arranged outside a housing of the tomography device, since, owing to the inclined beam guidance, the x-ray fan emitted at a circumferential point of the housing undergoes, on its way to the object and through the latter, such a large axial change in position that it runs past the region of the device housing opposite the beam source point.

The invention will be explained in more detail below using exemplary embodiments with reference to the drawing, in which.

Figure 1:
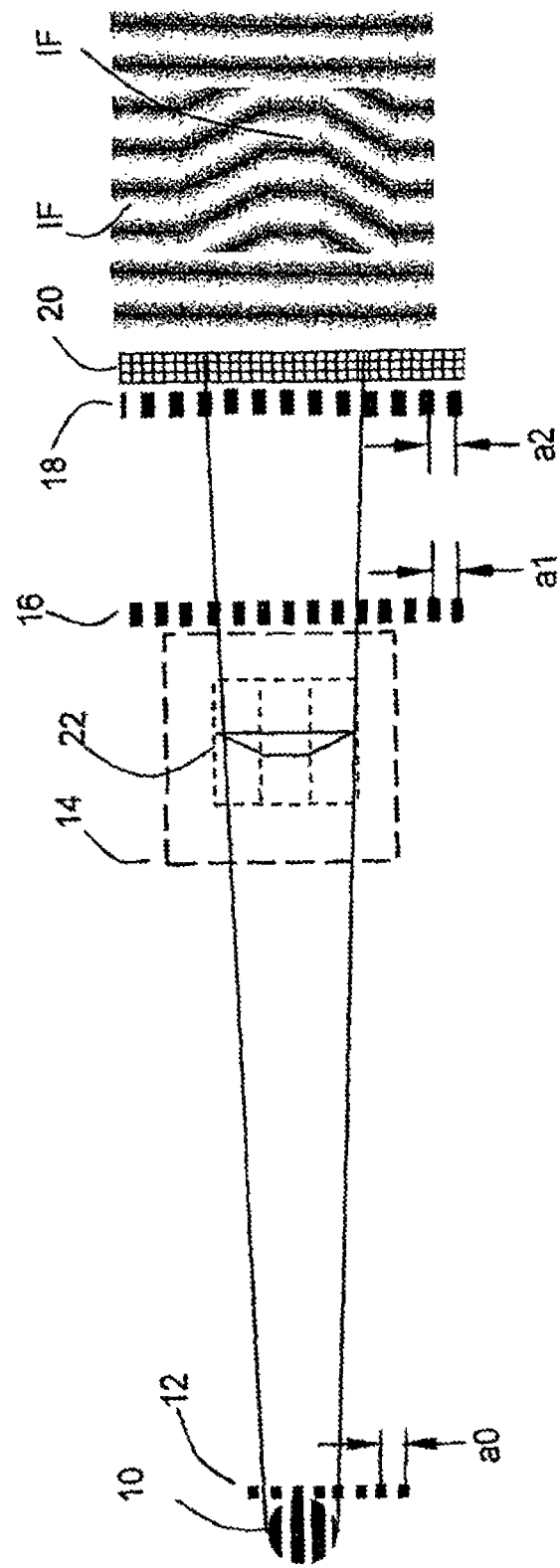
FIG. 1 shows a schematic representation, with the aid of which the principle of operation of phase contrast x-ray tomography is explained using a simple example, with an interference pattern as generated by a square test structure of trapezoidal cross-section being illustrated.

FIG. 1 shows the basic structure of a phase contrast x-ray tomography device. An x-ray source 10, which provides x-ray light of different wavelength which is not coherent, is also shown in FIG. 1. Arranged behind the x-ray source 10 is a coherence grating 12, which removes quasi-coherent x-ray light from the light of the x-ray source 10.

Such a coherence grating 12 is not necessary if the x-ray source 10 has a very small emission point, adapted to the Talbot condition, or a corresponding stripe structure ao.

An examination region 14 is bounded by a square represented by dashes.

Situated behind the examination region 14 is a phase grating 16, and at the Talbot distance from the latter there is provided an amplitude grating 18. All the aforementioned gratings are structures which are effective for x-rays and satisfy the Talbot condition.

Arranged behind the amplitude grating 18 is a ring-shaped detector strip 20, also referred to hereinbelow as the detector strip 20, the longitudinal direction of which coincides with the main extension direction of the amplitude grating 18. In the case of the gratings 16, 18 illustrated, the individual rules are to be envisaged as being perpendicular to the drawing plane, following one another at a small spacing a1, a2. Typical rule spacings a1, a2 are less than 10 μm, preferably in the range from about 1 to about 3 μm.

An arrangement as shown in FIG. 1 produces in the plane of the detector strip 20 an interference pattern with light and dark stripe sections.

The interference pattern obtained with an empty examination region 14 is to be understood as a reference interference pattern for the empty examination region 14.

If a phase object 22 is placed in the examination region, the interference pattern changes. The differences in the light and dark stripe can be converted into electrical signals by the detector strip 20, and these signals can then be converted into a phase image. The edge contour of the phase object 22 is indicated by dashes in FIG. 1 in a manner tilted into the drawing plane. The interference pattern IF too is rotated into the drawing plane for illustration purposes.

Typically, the interference pattern shown is obtained by a plate with trapezoidal cross-section, as shown in FIG. 1. By comparison with the reference image, the phase object 22, which is transparent to x-rays per se can now be recognized.

If the phase object 22 is removed from the x-ray path, the interference pattern, which are found in the vicinity of the phase image pass right through also in that region in which the image of the phase object 22 was previously situated.

Figure 2:
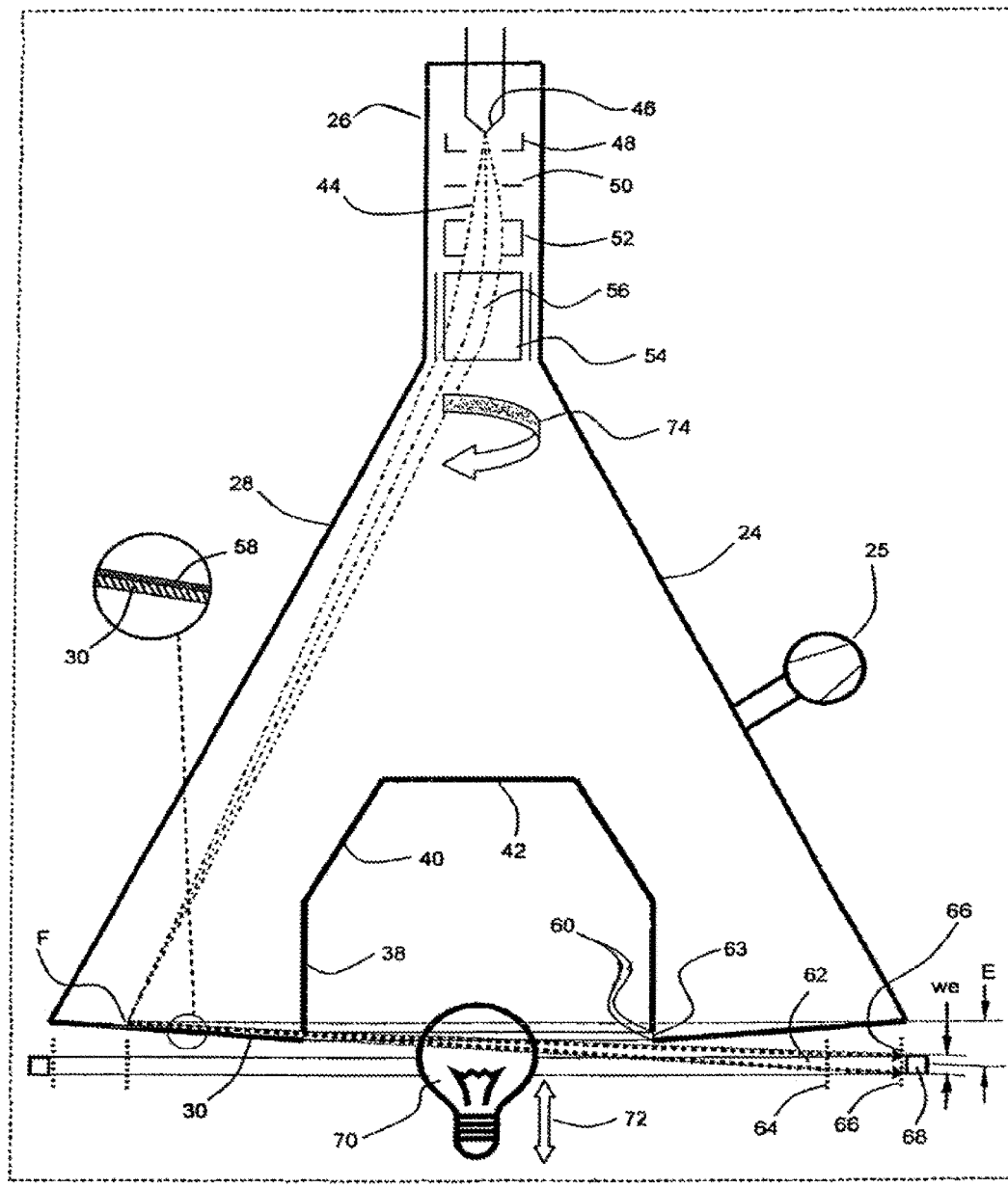
FIG. 2 shows a schematic axial section through a phase contrast x-ray tomography device.

FIG. 2 shows a tomography device with a circulating x-ray emission point F. A target ring 58 has the shape of a truncated cone with the vertex facing downwards and lying on the device axis.

The x-ray tomography device has a gas-tight evacuated housing 24, also referred to hereinbelow as the housing 24, which includes a housing neck 26, an outer conical housing wall 28, i.e., the housing wall 28, an obliquely downwardly and inwardly sloping bottom wall 30, i.e., the bottom wall, a cylindrical housing wall 38, i.e., the housing wall 38 running axially back again, an upwardly converging truncated-cone shaped housing wall 40, i.e., the housing wall 40 adjoining the latter, and an end wall 42.

The entire inner space of the housing 24 is evacuated to a pressure of less than $10^{-5}$ mbar. This vacuum can be produced both by hermetic tightness and by specific pumping with a mounted-on vacuum pump 25 during operation.

Situated inside the housing 24 is an electron gun 44. The latter includes, schematically represented, a heated cathode 46, a control electrode 48, an accelerating electrode 50, an electrostatic lens 52 and a deflecting coil 54. Alternatively, an electrostatic deflecting unit which comprises a deflecting plate capacitor may also be used.

An electron beam 56 is represented in dashes by its centre line and its envelopes.

Arranged on the bottom wall 30 is a ring-shaped target 58, also referred to hereinbelow as the target 58, which can be made from material which is customary for x-ray targets.

The target 58 has the shape of a widely opened truncated cone with an opening angle of the cone vertex of about 160°.

Situated at the junction between the bottom wall 30 and the cylindrical housing wall 38 is a small gap 60 which is closed by an x-ray window 63. The latter extends over a full 360°, so that x-ray light 62 which is formed on impingement of the electron beam 56 on the target 58 can emerge, in any angular position, produced by the deflecting coil 54 or a deflecting capacitor, of the focal point F relative to the axis of the housing 24, through a corresponding region of the x-ray window 63.

The x-ray light 62 is depicted only in its usable fan shaped region which is predetermined by the height of the x-ray window 63. Of course, from the point of impingement of the electron beam 56 on the target 58, further x-ray light also radiates into the upper half-space, but this light is absorbed by the housing wall 28, bottom wall 30, cylindrical housing wall 38, housing wall 40, and end wall 42 of the housing 24 and not used for measurement purposes. To this end, the housing 24 may optionally be surrounded with additional shielding material.

The x-ray window 63 may, at the same time, be chosen from a material which absorbs undesired parts of the x-ray spectrum. These are in particular long-wave portions of the continuous portion of the spectrum. As narrow-band a spectrum of the x-ray light as possible is desired, the average wavelength of which together with the adjustable x-ray diffraction structures, here a ring-shaped phase grating 64, also referred to hereinbelow as the phase grating 64, and a likewise ring-shaped amplitude grating 66, i.e., the amplitude grating 66, satisfies the Talbot condition.

Owing to the conical shape of the target 58 and owing to the fact that the point of impingement of the electron beam 56 on the target 58 in FIG. 2 is higher than the x-ray window 63, the x-ray fan used for measurement purposes is directed obliquely downwards and can, on the opposite side of the bottom wall 30 located on the right in FIG. 2, pass through under this wall.

Figure 3:
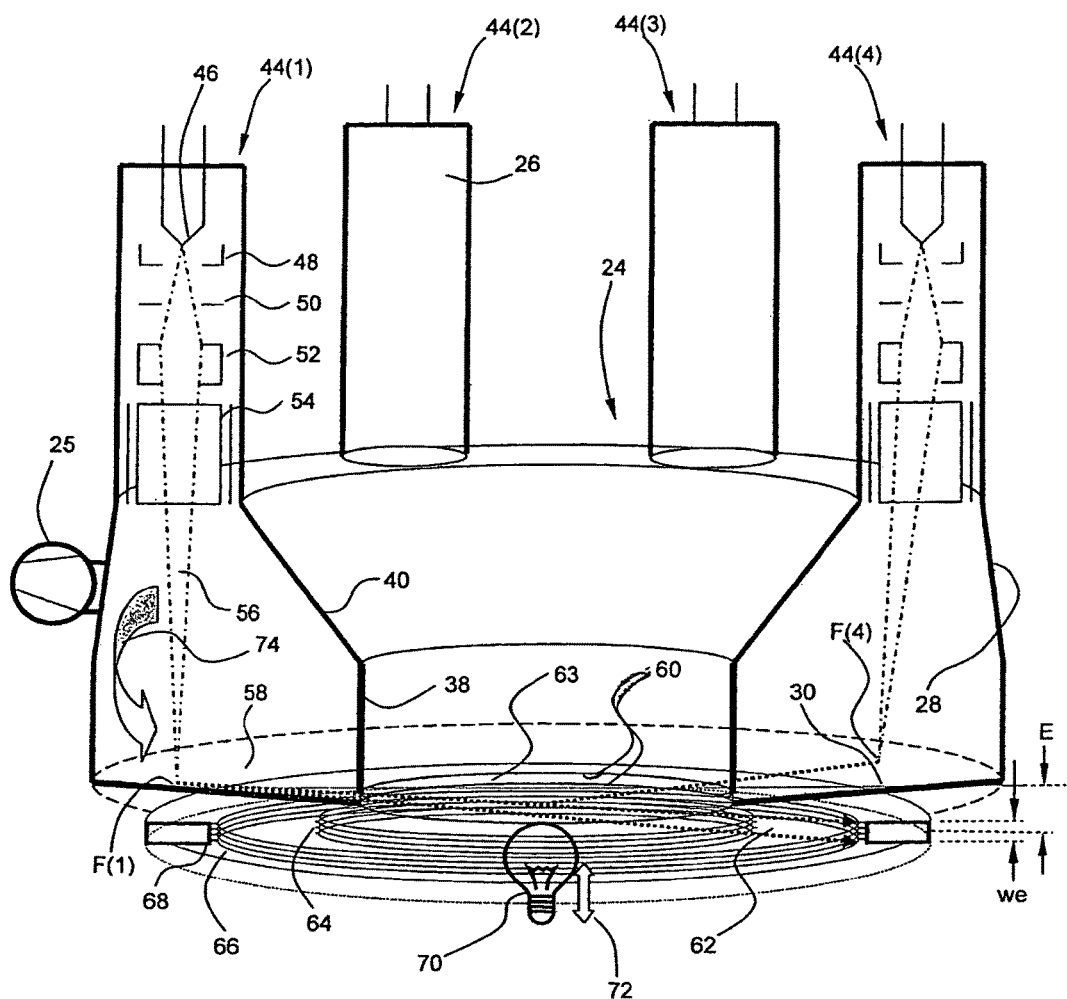
FIG. 3 shows an axial half-section through a modified phase contrast x-ray tomography device, which has a plurality of electron guns and is suitable for long objects.

If the x-ray window 63 is a little higher than in FIGS. 2 and 3, the bottom wall 30 can have a lower turned-up circumferential wall at its radially inner end.

Below the bottom wall 30 there is arranged, concentrically with respect to the housing axis, a ring-shaped phase grating 64 which is indicated by dashes. Radially outside the phase grating 64 there is situated coaxially a likewise ring-shaped amplitude grating 66. And around the ring-shaped amplitude grating 66 there is arranged a ring-shaped detector strip 68, also referred to hereinbelow as the detector strip 68.

The ring shaped detector strip 68 comprises in the strip longitudinal direction detector elements following one another at a very small spacing, the spacing of which is smaller than the period of interference patterns which are produced by the phase grating 64 and the amplitude grating 66 in the region of the detector strip 68. In the direction of rotation (axial direction of the device), the detector strip 68 comprises a smaller number (e.g. 8, 16 or 32) of detector elements following one another at an equal small spacing. The detector strip 68 thus forms as a whole a ring-shaped detector area with a plurality of 100,000s of detector pixels in a ring row, which may comprise for example about 250,000 detector elements following one another in the circumferential direction (for a whole-body phase contrast tomography device of about 80 cm clear width), if one detector element is provided for each rule of the x-ray gratings. 8, 16 or 32 of such lines of detector elements are stacked axially one after the other at the spacing of the detector elements. How many rows are provided one after the other in the axial direction is a question of the optimization of the detectors.

In principle, one detector ring row is sufficient. If detectors with pixel sizes of a fraction of the desired spatial resolution are available, the phase measurement can be extended to a plurality of pixels, e.g. 3×3 or 4×4 pixels per resolution point. If the geometrical resolution of the entire arrangement is limited by other factors anyway (e.g. focal spot size and magnification), a 3- to 4-row detector per resolution row is recommended. A further increase in the number of rows is expedient on account of better utilisation of the x-ray radiation, but is only possible if the grating lamellae, with increasing axial distance from the path plane of the focal point F, are correspondingly inclined, which in turn increases the outlay on the grating arrangement.

As will be described in more detail later, it is favourable for the measurement of the interference figures per se if the spacings of the detector elements are as small as possible. A larger number of sampling points per stripe-pattern period is then obtained, from which the course of the sine-wave form in the intensity distribution can be directly calculated.

If there are a smaller number of sampling points, possibly only one detector element per resolution cell or fewer detector elements than resolutions cells, the phase measurement of the wavefront has to be made possible by displacing one of those structures responsible for producing the interference image (x-ray source 10, coherence grating 12, phase grating 16, amplitude grating 18) by very small distances amounting to fractions of the spacing of two grating lines, in order to obtain, when small displacements of a diffraction-relevant components are known, additional information about the intensity profile, whereupon these additional measuring points can be used as additional sampling points for adapting a sine curve and for determining the phase position of this sine curve.

This is described in more detail later. Here it should be initially assumed that the division of the detector strip 68 is sufficiently small to be able, without the above-mentioned relative movements by very small distances, to measure the interference pattern sufficiently precisely to determine the phase position of the wavefront therefrom.

The x-ray grating, i.e. the phase grating 64 and the amplitude grating 66, are shown in the drawing as gratings which have layers, made from x-ray-transparent material and x-ray-absorbing material, following one another alternately in the direction of the device axis (or even oriented in the direction of the opposite emission point path in the case of particularly wide strips).

All that is important for the purposes of the invention is that the two x-ray gratings together produce an interference image. Such an interference image can also be obtained with x-ray gratings in which the layers made from transparent material and absorbing material following one another alternately are stacked periodically one after the other in the circumferential direction.

As can be seen from the drawing and can be derived from the geometry of the x-ray window 63 and the point of impingement of the electron beam 56 on the target 58, the x-ray light 62 has the shape of a very slightly diverging, very flat, fan-shaped x-ray beam.

The fan-shaped x-ray light 62 is distinguished with regard to its course and its geometry by the following angles: An angle E, at which its plane of rotation is inclined relative to a plane which is situated transversely to the device axis. Furthermore, an elevation fan angle we, which represents the spread angle of the fan in an axial sectional plane. Furthermore, a spread angle of the fan in the circumferential direction wu, which represents the spread angle of the fan in the plane of rotation. These different angles are marked in FIGS. 2 to 4. In the other figures they are only partially marked. In the vicinity of the axis of the housing 24 there is shown in each case an examination object 70, also referred to hereinbelow as the object 70, (by way of example in the form of a light bulb) with its preferred movement direction 72.

The x-ray light 62 passes through the examination object 70, with the latter in a preset position, in exactly one sectional plane per detector resolution row. In order to be able to examine other layers of the examination object 70, the latter can be moved preferably in the axial direction by a schematically indicated drive 72. Alternatively, x-ray tomography device can be moved.

From the above description of the device according to FIG. 2, it can be seen that by appropriate energizing of the deflecting coil 54 the electron beam 56 can be moved on a circular path about the axis of the housing 24, as indicated in the drawing by an arrow 74. Upon this movement, the point of impingement F of the electron beam 56 on the target 58 then travels onto a circle which is concentric with respect to the housing axis, and the x-ray light 62 then emerges at an appropriate angular orientation from the x-ray window 63.

FIG. 3 shows a modified tomography device. Components which functionally correspond to components already described with reference to FIG. 2 are provided with the same reference symbols and do not need to be described again in detail.

In the tomography device according to FIG. 3 there are provided a plurality of electron guns 44 which have a similar structure to the electron gun shown in FIG. 2. The electron guns 44 according to FIG. 3 are, however, now distributed at a regular spacing over the circumferential extent of the housing 24, so that the electron beams 56 generated respectively by them have only to sweep over a partial region of the circumferential extent of the ring-shaped target 58. Through sequential triggering of the different electron guns 44, altogether the entire circumferential extent of the target 58 is then covered, it also being possible to use a plurality of electron guns simultaneously, provided that their x-ray beam fans do not overlap on the detectors.

In the arrangement according to FIG. 3, the different electron guns do not need to be activated successively in the circumferential direction. The electron guns may also be activated in a different order, which may be advantageous as regards heat problems in the target 58. It is advantageous but not absolutely essential, merely, for all the electron guns 44 to have been activated exactly once in this way in a preset period of time (scanning cycle) and for their electron beam 56 to have been moved on the assigned arc-shaped segment of the entire circumferential extent of the target 58.

Figure 4:
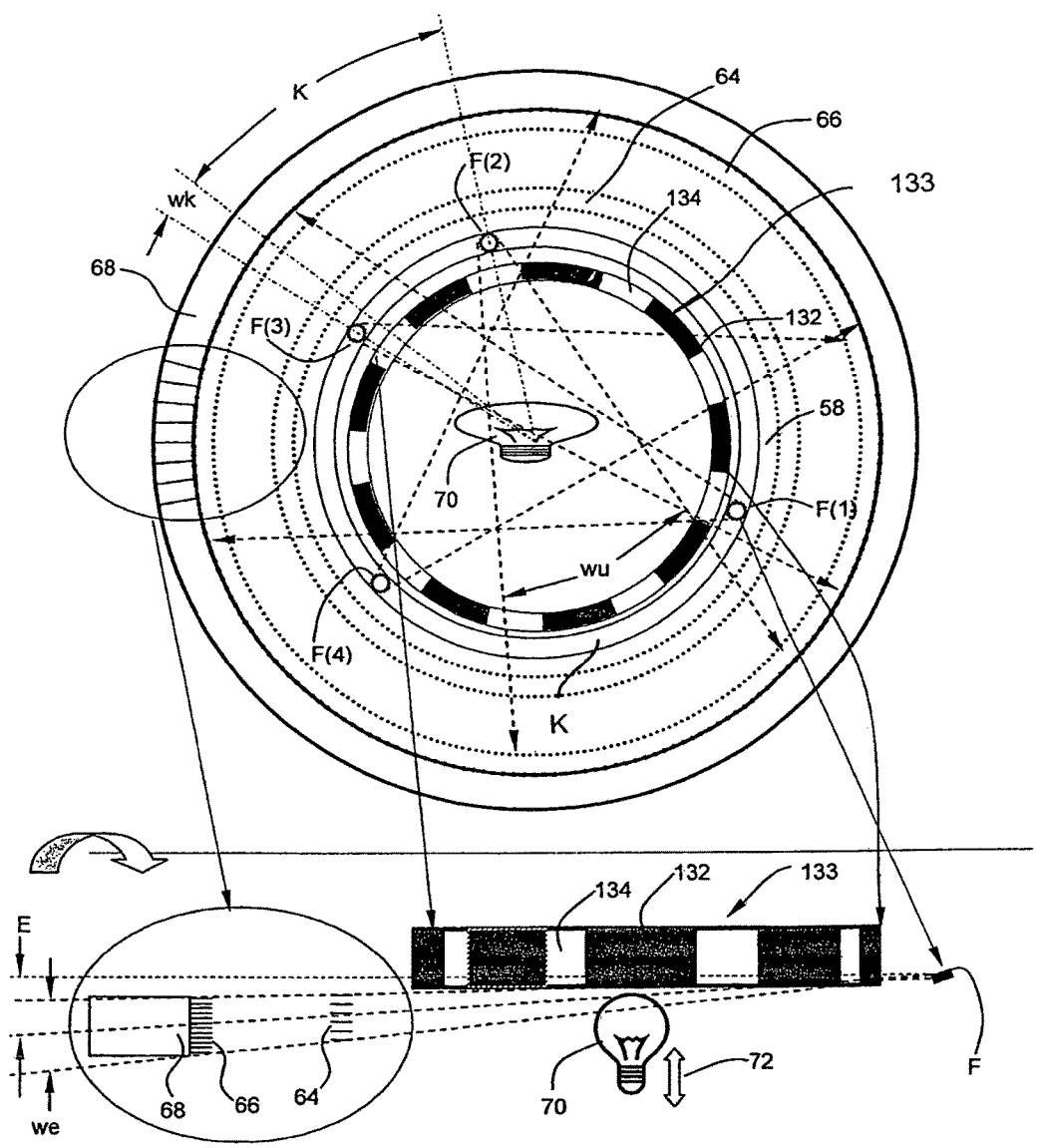
FIG. 4 shows an axial plan view of beam boundaries and x-ray gratings of a phase contrast x-ray tomography device, with some elements folded over into the plane of the drawing (upper section of the figure), and a lateral view of the tomography device (lower part of the figure)

FIG. 4 shows a plan view of the bottom section of the tomography device, with the angular extent of the x-ray fan in the direction perpendicular to the device axis (examination plane) and the fanning of the x-ray light in the vertical direction (elevation fanning) being shown in more detail. Furthermore, in the drawing a few rules are indicated in the detail representation for the phase grating 64 and the amplitude grating 66. The structure of these ring-shaped x-ray gratings will be explained in more detail later with reference to FIGS. 14 and 22. The point of impingement of the electron beam 68 on the target 58 is denoted by F in FIG. 4. K stands for the track on which the focal spot F of the electron beam moves over the target 58.

A segmented screen configured as a screen grating is denoted by 133 in FIG. 4. It comprises a large number of screen bars 132 which follow one another at a small spacing in the circumferential direction and between which screen windows 134 remain.

The screen 133 is arranged in a spatially fixed manner at a small spacing on the inner or outer side of the x-ray window 63 and the electron beam 56 is displaced, by suitable excitation of the deflecting coil 54, in increments on the target 58 in such a manner that the focus F is in each case radially aligned with the centre of one of the screen windows 134.

For each given moment in the examination plane there is thus an x-ray beam whose width is predetermined by the width of the screen window 134 and the path radius of the electron beam point of impingement F.

A specific eccentric position of the examination volume can be achieved too by angle of rotation-dependent displacement of the electron beam point of impingement F relative to the centre of the screen window 134.

The evaluation of the output signals of the detector strip 68 is performed, when using the screen bodies according to FIG. 3 and according to FIG. 4, such that in each case a partial region of the detector strip 68 on which usable interference patterns are obtained is activated or its output signal evaluated. The selection of this region may also be performed with evaluation of the deflecting signals for the deflecting coil 54.

By narrow lateral (circumferential-angle) limiting of the x-ray beam in the examination plane, the dose for the patient is reduced, and in particular in an embodiment according to FIG. 3 the image acquisition speed is increased.

Figure 5:
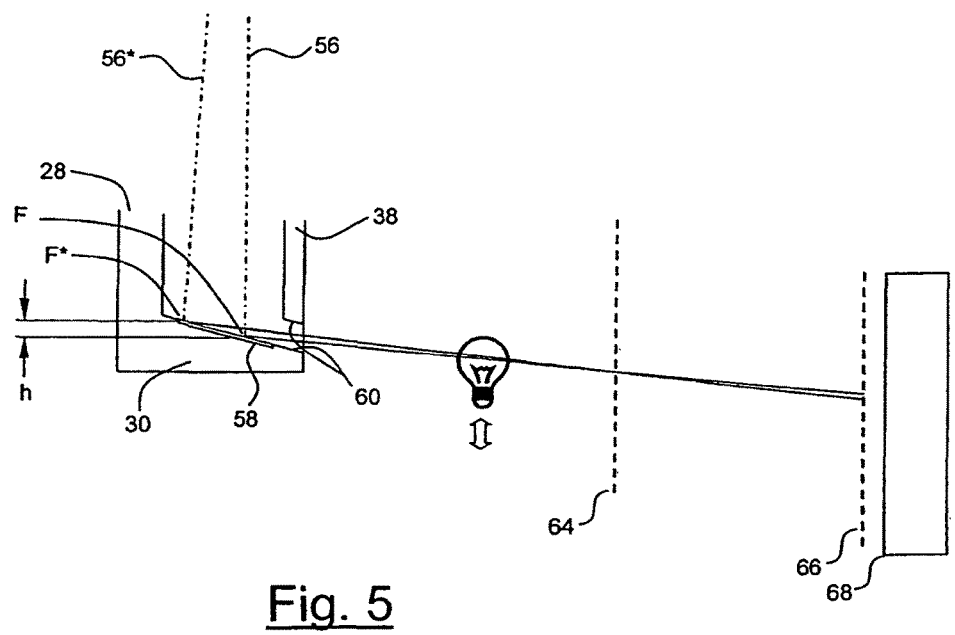
FIG. 5 shows an axial partial section through target ring and diffraction grating of a further phase contrast x-ray tomography device.
Figure 6:
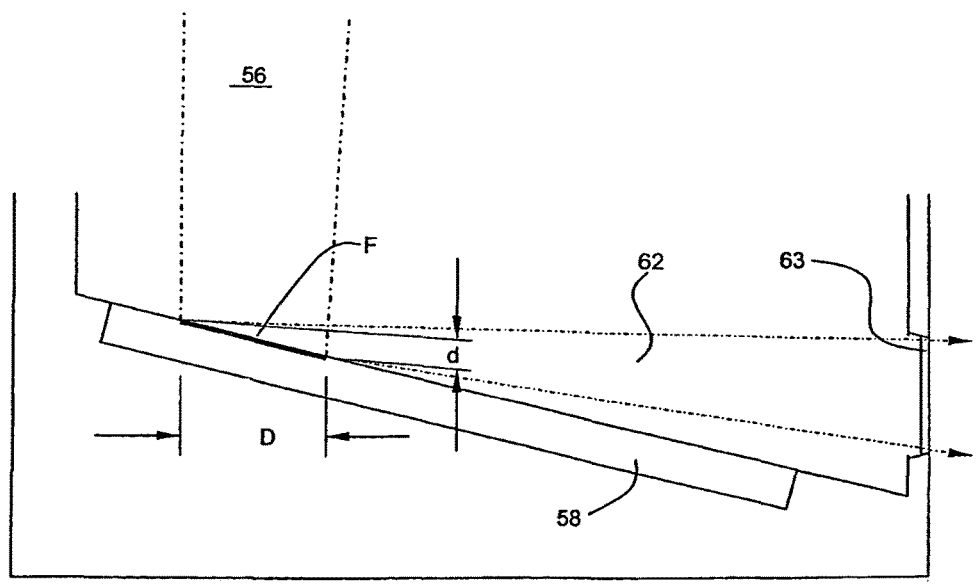
FIG. 6 shows an enlarged view of the target ring according to FIG. 5.

FIGS. 5 and 6 show again schematically the beam path between the ring-shaped gap 60 and the detector strip 68 on an axially enlarged scale.

It can also be clearly seen from these figures that the inclination of the target 58 results in a reduction of the seen size of the punctiform x-ray light source formed by the focus F of the electron beam 56 on the target 58. If the cross-section of the incident electron beam 56 has the size D, only a fraction d of this size appears when seen in the axial direction.

In this way, it is possible to examine an object in very thin layers and at the same time improve the spatial coherence in the axial direction such that the coherence grating 12 illustrated in FIG. 1 may optionally be dispensed with and nevertheless the Talbot condition satisfied.

Figure 7:
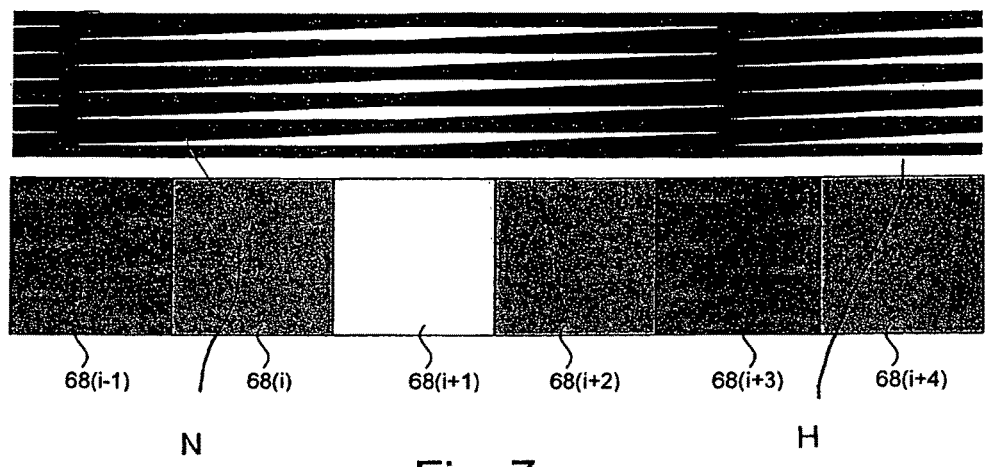
FIGS. 7 to 11 show various interference patterns which result for different grating constants of the x-ray gratings and different tilting of the same relative to one another.

FIG. 7 shows schematically an interference pattern as obtained in the light-sensitive area of the detector strip 68 for a preset relative position of phase grating 64 and amplitude grating 66. Relative position is to be understood here as both the distance perpendicularly to the grating surface and the inclination of the grating lines of the two gratings with respect to one another.

In the exemplary embodiment illustrated, the interference pattern comprises horizontal stripes H lying equally spaced one beside the other. A second group of stripes running at a small angle inclined to the stripe H is denoted by N. The stripes H and N in FIG. 7 form, when seen additively placed one above the other, regions with a large black portion and regions of high brightness, which roughly speaking each have a lozenge-like structure.

Shown below the stripe pattern as grey-scale images are the associated brightness values of detector elements 68$i$, 68$i$+1 to 68$i$+6.

The brightness profile from left to right corresponds to a sinusoidal profile with a fundamental value, since no negative brightness can occur. The amplitude and phase position in these six detector elements can now be calculated by mathematical methods (fitting, Fourier transformation).

Figure 8:
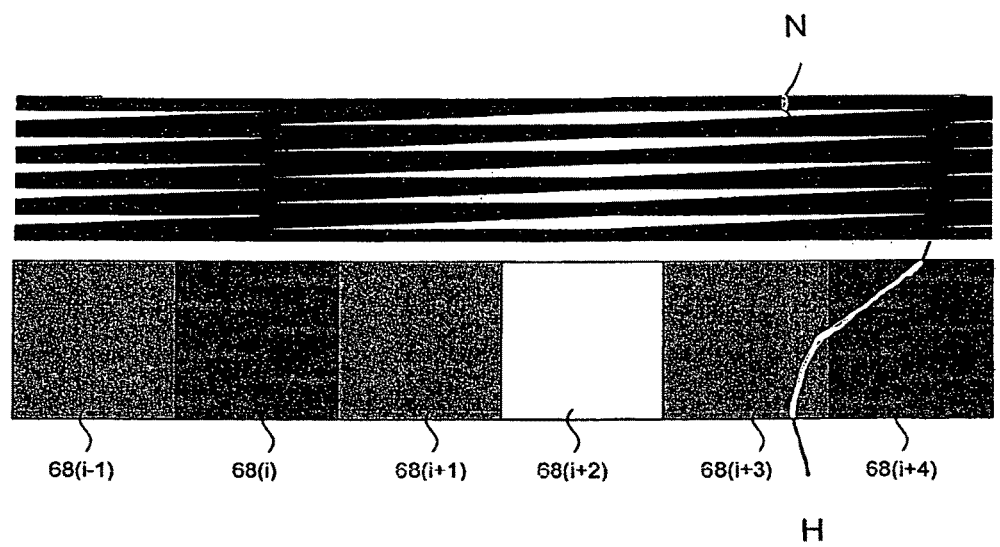

FIG. 8 shows a similar image, in which however the phase position between the interferences, which are obtained by phase grating and amplitude grating, is changed. Such a change of the phase position can be obtained by a displacement of the object and/or a displacement of the x-ray light source and/or a displacement of the phase grating and/or a displacement of the amplitude grating and/or by a tilting of the phase grating and/or a tilting of the amplitude grating.

It can be seen that the changed interference pattern also results in a changed brightness distribution in the brightness profile shown below the interference pattern, to be precise in the form that the sinusoidal brightness distribution has shifted by one detector pixel to the right.

Figure 9:
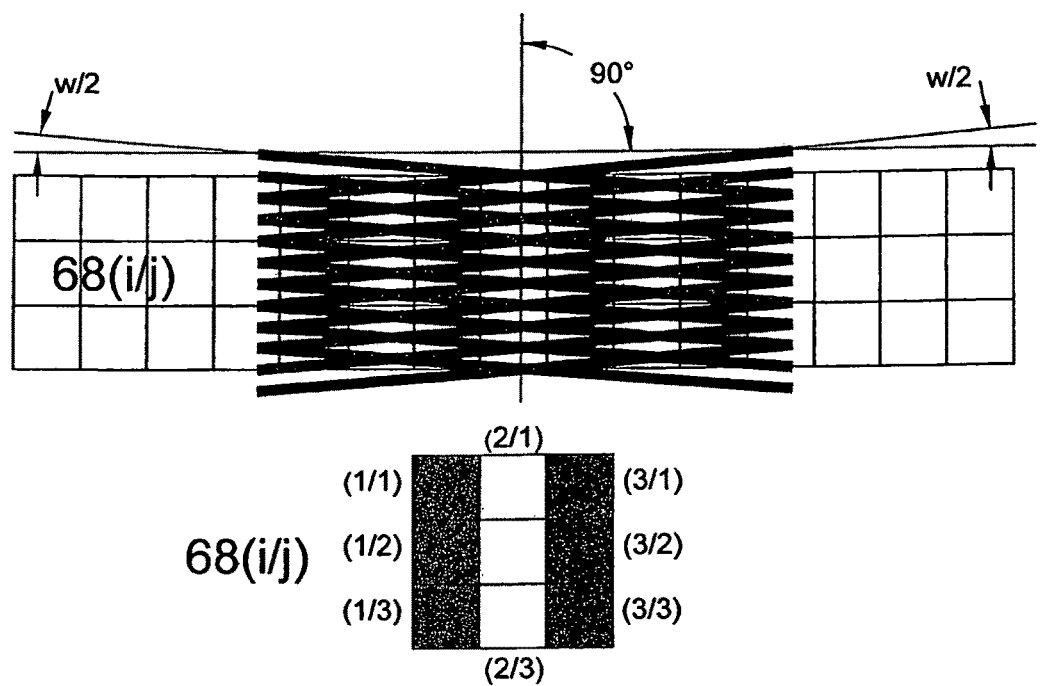
Figure 10:
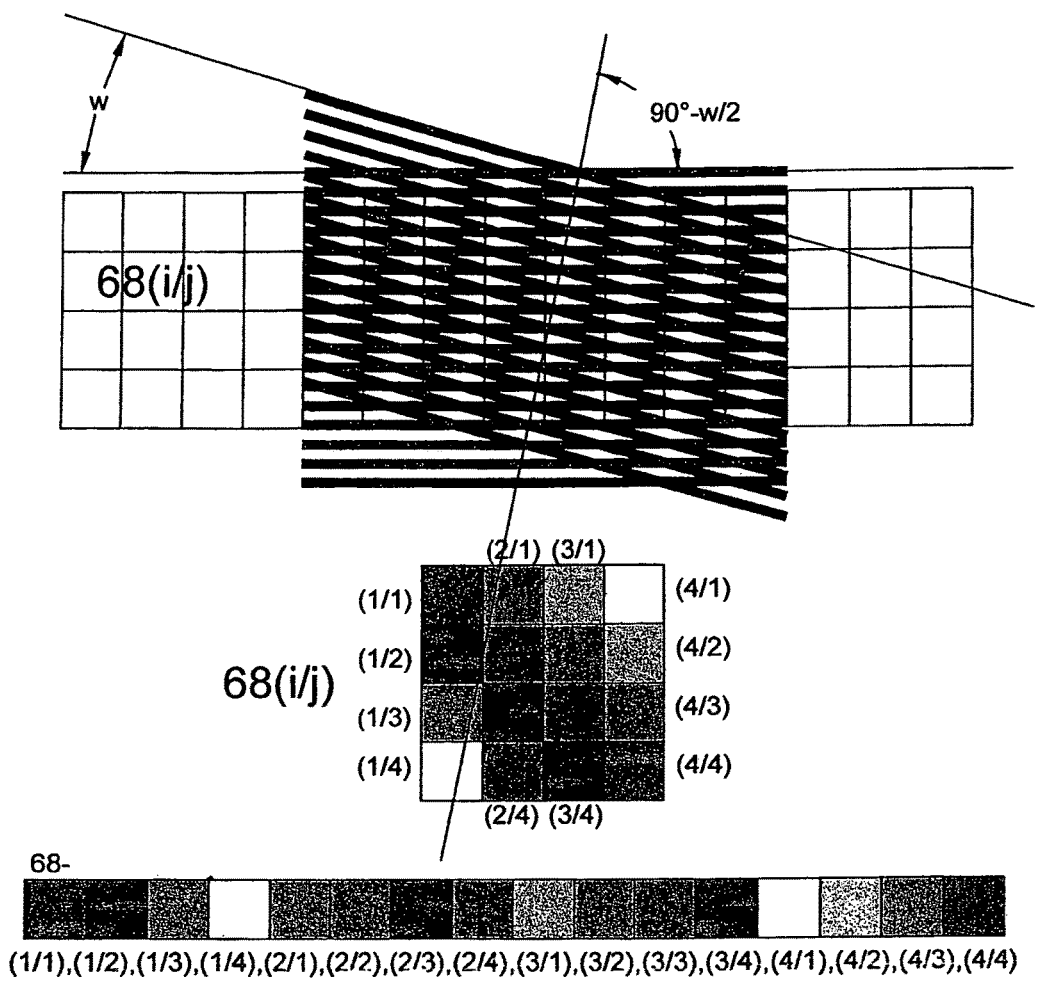
Figure 11:
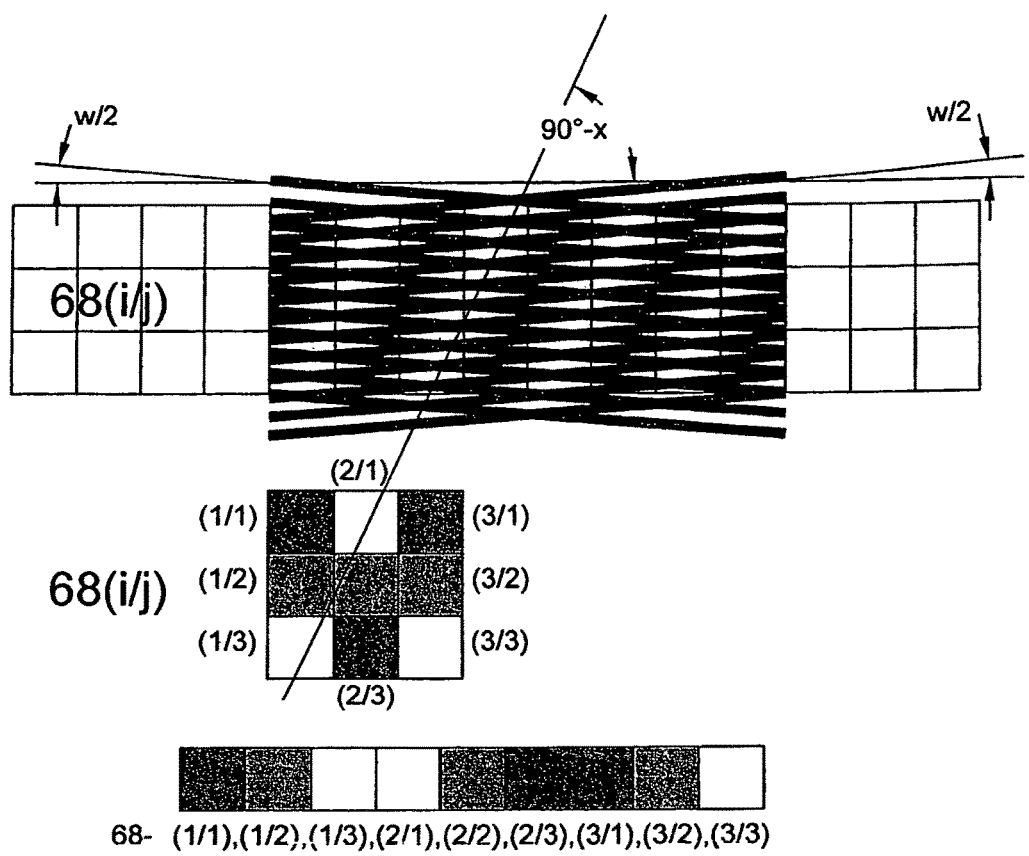

If all six pixels 68$i$ to 68-$i$+4 which belong to a resolution pixel are now considered, it is possible to count back to an altered phase position, which is caused e.g. also by an object in the x-ray beam. If a detector arrangement with only one row of detector pixels is used, a very shapeless, elongated resolution pixel in the form of 6×1 detector pixels is obtained. In FIGS. 9 to 11 it is therefore illustrated how the phase measurement of a rather square resolution pixel can be carried out e.g. from 4×4 or 3×3 detector pixels.

FIG. 9 shows a modified geometry, in which the phase grating and the amplitude grating are tilted by opposite and equal angles relative to a reference direction. This arrangement would likewise be suitable for an elongated resolution pixel, since the upper and lower pixel row is identical to the middle row and the phase position of the sinusoidal oscillation can be actually determined from only three sampling points.

According to the sampling theorem, although this would be sufficient, in practice such x-ray images are, however, also distorted by noise, so that it would be better to evaluate more sampling points for determining the phase position. By suitable inclination of the gratings according to FIGS. 10 and 11, now all 16 and, respectively, 9 pixels of the 4×4 and, respectively, 3×3 pixel resolution pixel are approximately equally distributed in the sinusoidal period.

In the order (1/1), (1/2), (1/3), (1/4), (2/1), (2/2), (2/3), (2/4), (3/1), (3/2), (3/3) etc., a sinusoidal intensity distribution results, from which the phase position and amplitude can be determined as in FIGS. 7 and 8. It can be seen that by tilting the gratings an interference pattern which has a smaller period length in the horizontal direction is obtained. The period length is therefore adjustable by the tilting angle w. FIG. 11 shows a stripe pattern which is obtained by choosing slightly different grating constants for phase grating and amplitude grating. Otherwise, the arrangement of the gratings corresponds to that according to FIG. 9.

It can be seen that in this way the stripe pattern is "sheared" in the horizontal direction, and it can thus be evaluated equivalently to the stripe pattern in FIG. 10. By suitable choice of the tilting angles of the gratings and the grating constants, it is thus possible to adjust the interference pattern of each resolution pixel such that in each associated detector pixel array of almost any desired choice (e.g. 3×4), a sinusoidal oscillation can be readily adapted with all associated detector pixels. By specifically different grating constants, it is even possible to arrange one of the gratings absolutely horizontally without disadvantages, as shown in FIGS. 12 to 16.

Figure 12:
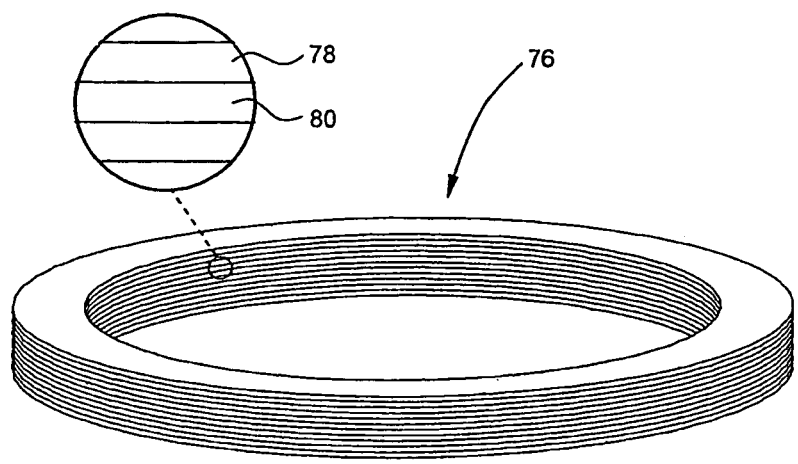
FIG. 12 shows a perspective view of a first rotationally symmetrical x-ray grating structure.

In FIG. 12, a ring-shaped x-ray grating 76, also referred to hereinbelow as the x-ray grating 76. It consists of an axial succession of layers 78, 80, which consist of different material. The difference in the materials may lie in the velocity of propagation of x-ray light, and then the x-ray grating 76 is a phase grating. The difference in the layers 78, 80 may, however, also lie in the absorption of x-ray light, and then the x-ray grating 76 is an amplitude grating.

Typically, x-ray gratings are produced such that there is a basic structure which is transparent to x-ray light and is provided with a fine groove pattern. This basic structure is then thinly coated with another material. At the groove base, which is situated perpendicular to the direction of propagation of the x-ray light, this thin material influences the x-ray light only slightly, since the layer there is very thin. By contrast, in the regions of the groove walls, the x-ray light has to pass through the vapour-deposited material over a long way, so that there is a great influence.

The x-ray grating thus has wide regions in which the light is only influenced a little in terms of phase and in terms of amplitude, and narrow regions which greatly shade the light, or cause a large phase change.

The ring-shaped x-ray grating 76 according to FIG. 12 is macroscopically in one piece.

Such ring-shaped x-ray gratings may, however, also be composed of a plurality of segments.

Figure 13:
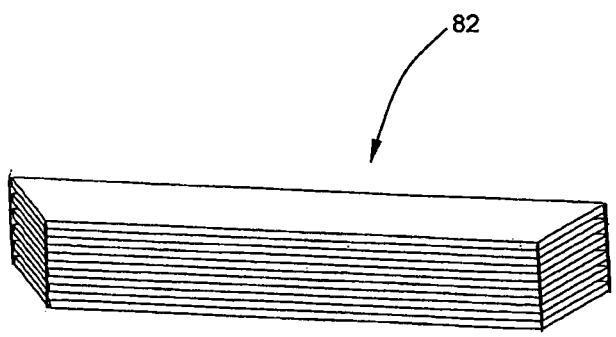
FIG. 13 shows a perspective view of a segment of a polygonal x-ray grating structure.
Figure 14:
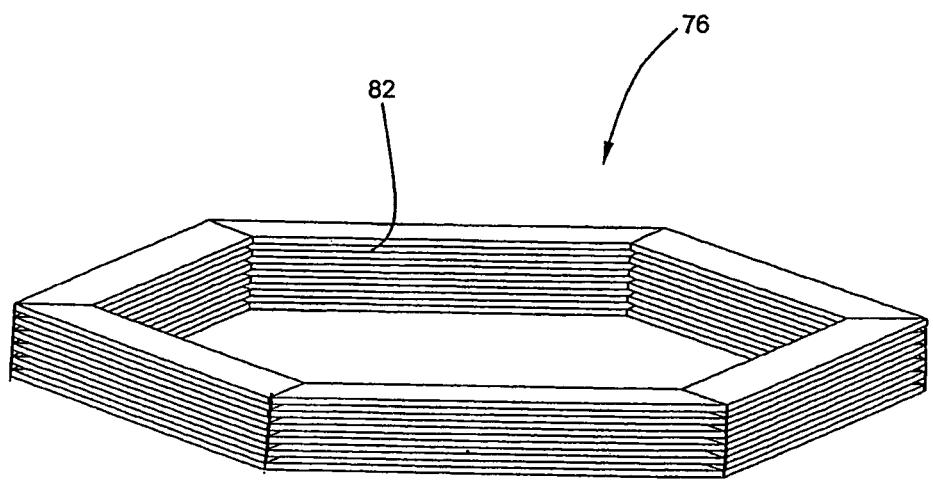
FIG. 14 shows a perspective view of a further polygonal x-ray grating structure.

FIG. 13 shows a first such bar-shaped ring segment 82, also referred to hereinbelow as the segment or segments 82, having end faces beveled at 30°. Such bar-shaped ring segments 82 can be assembled to form a hexagonal ring, so that an x-ray grating 76 as shown in FIG. 14 is obtained.

Figure 15:
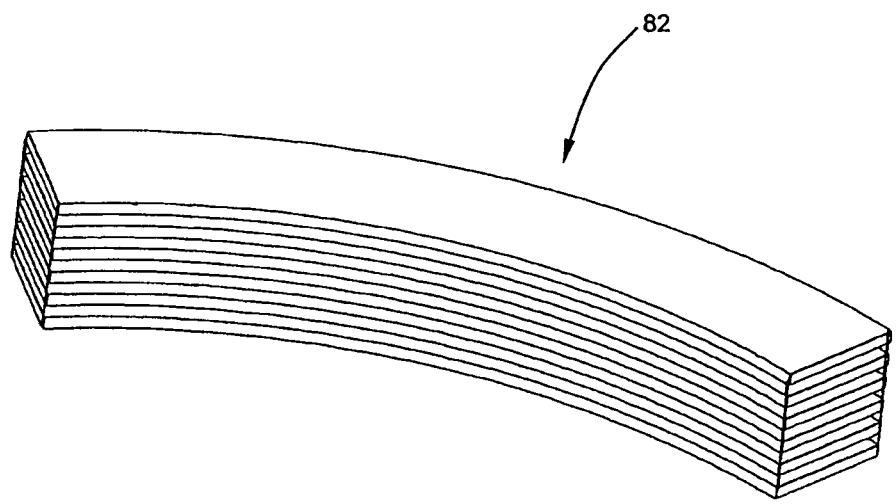
FIG. 15 shows a segment of a further rotationally symmetrical x-ray grating structure.
Figure 16:
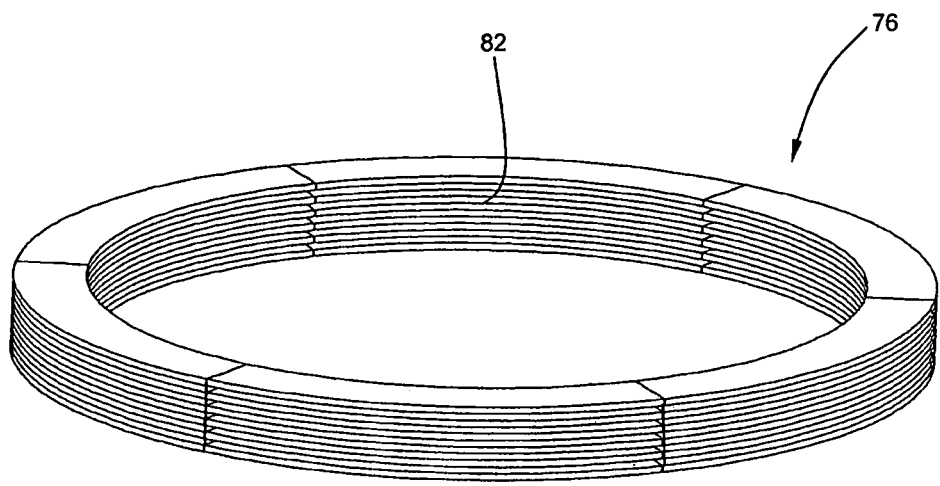
FIG. 16 shows a perspective view of a further rotationally symmetrical x-ray grating structure, which is composed of arc-shaped segments.

Similarly, using circular-arc-shaped ring segments 82 with radial end faces as illustrated in FIG. 15, a ring-shaped x-ray grating 76 shown in FIG. 16 can be assembled.

Figure 17:
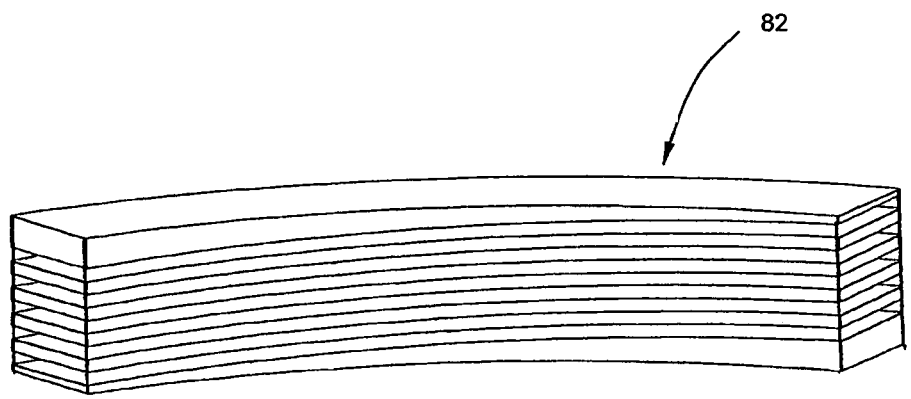
FIG. 17 shows a similar view to FIG. 15, in which however the transmission regions of the grating structure are arranged along slightly inclined helical lines.

In order to have an x-ray grating 76 in which the grating lines run at a slight inclination to its front faces, a ring segment 82 as shown in FIG. 17 can be produced. In this segment, the grating lines are inclined obliquely to the ring axis.

Figure 18:
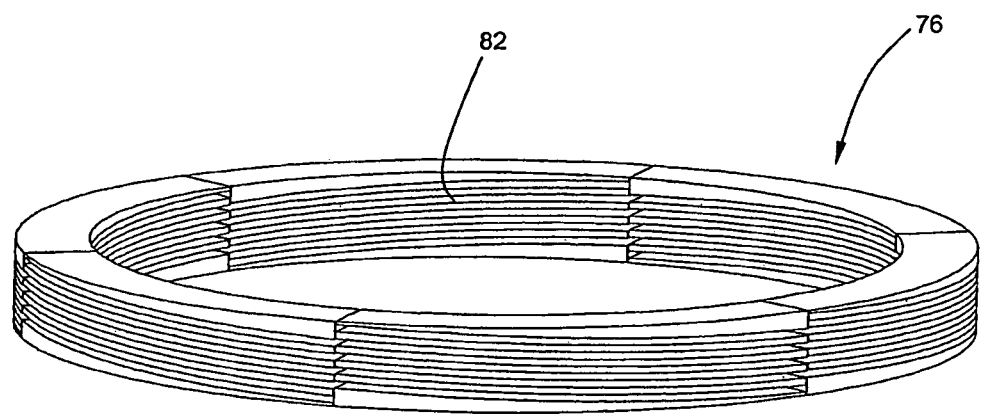
FIG. 18 shows a perspective view of a macroscopically cylindrical x-ray grating structure with helically running rules.

Using segments 82 according to FIG. 17, a ring-shaped x-ray grating 76 as shown in FIG. 18 can then be produced. It can be seen that the layers 78, 80 form a multi-start helix.

In such an x-ray grating 76, the outer end faces can be used as adjusting and fitting surfaces which cooperate with shoulders running transversely to the device axis. It is thus not necessary to form seating surfaces of the housing at a preset small angle to the device axis in order to tilt grating lines in this way. Nor is there any need to provide adjusting means to adjust the inclination of the grating lines.

Figure 19:
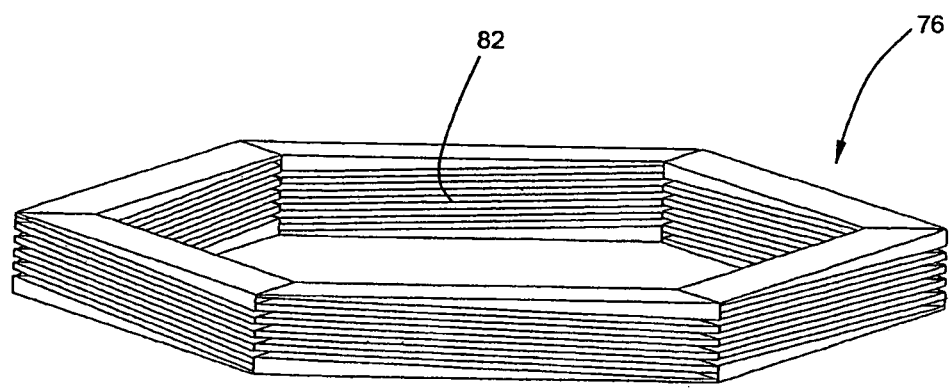
FIG. 19 shows a similar view to FIG. 18, in which however the segments of the x-ray grating structure are rectilinear.

FIG. 19 shows a similar x-ray grating 76 to FIG. 18, but which is configured as a hexagonal ring.

Figure 20:
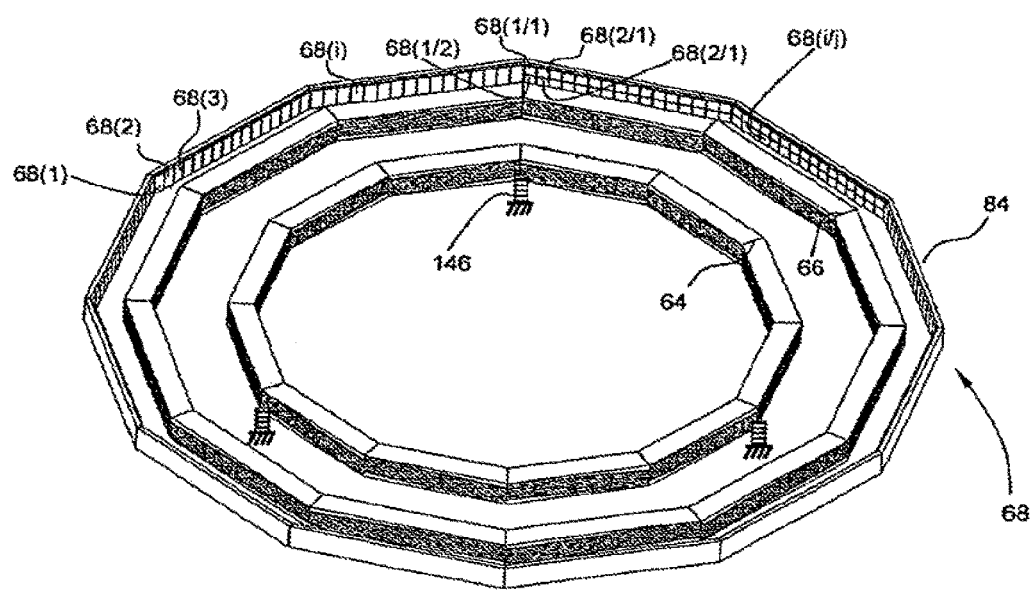
FIG. 20 shows a perspective view of polygonal x-ray grating structure as illustrated in FIG. 19, but with this one being additionally surrounded by a polygonal partially multi-row detector structure.

FIG. 20 shows an inner phase x-ray grating 64 and a ring-shaped amplitude x-ray grating 66 surrounding the latter at a spacing, the gratings both being configured similar to the x-ray grating 76 but having twelve segments correspondingly bevelled at the circumferential ends. In this way, x-ray gratings and detector rows or strips having a large diameter can be assembled from smaller units.

Around the ring grating is shown the detector strip 68, which is likewise constructed from straight detector segments 84, the ends of which are bevelled at 15°. It has detector element rows 68-1, 68-2, . . . 68-$i$, . . . .

It is easily conceivable in FIG. 20 now to combine 3- or higher-row detector strips, a grating ring according to FIG. 19 and a grating ring according to FIG. 14 and to apply the evaluation method according to FIG. 10. Higher-row detector strips with pixels 68(1/1), . . . , 68(*i/j*) are perfectly appropriate here and can be used to provide several layers of the tomogram simultaneously. In particular, commercially available strip detectors even in the smaller dimension generally have 64 and more rows and an extent of more than 6 mm. With resolution pixels of for example 300 μm these are already 20 simultaneously measured layers. Also for the grating strips, a production in a width of 6 mm is far more economical than with a width of 0.3 mm. The assembly of the grating strips is thus also simplified.

When forming wider strips with customary dimensions greater than 10 mm, however, it must be taken into consideration that the orientation of the grating plates must, where necessary, also roughly point in the direction of the emission plane, because with the customary dimensions otherwise a so-called Venetian effect impairs or even destroys the grating effect. To this end, an additional pyramid-, cone- or sphere-like form of the grating rings is then necessary.

In this way, x-ray gratings and detector rows having a large diameter can be assembled from smaller units.

Figure 21:
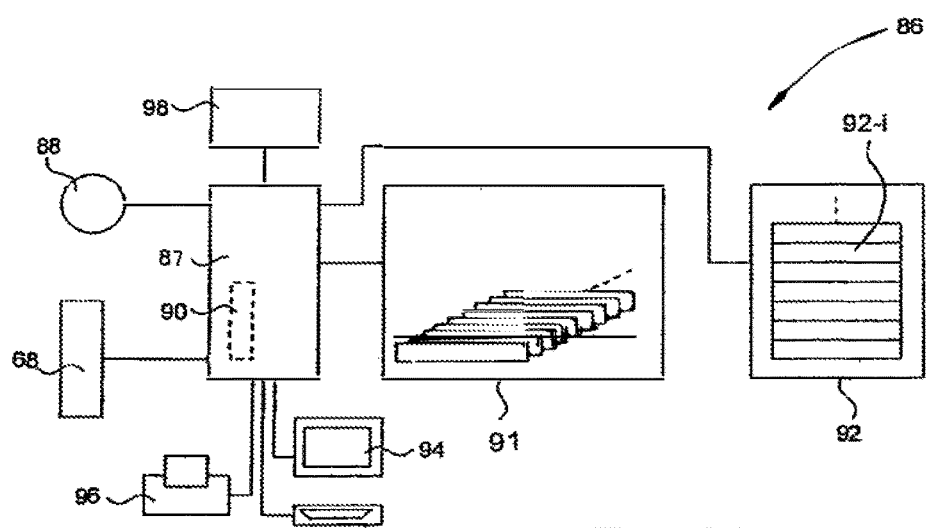
FIG. 21 shows the block diagram of an evaluation device of the x-ray tomography device.

FIG. 21 schematically illustrates an evaluating unit 86 which converts the output signals of the detector strip 68 into a phase image of the object 70. The evaluating unit 86 has a programmable processor 87 which cooperates with a position sensor 88 which provides a signal corresponding to the position of the electron beam 56 in the circumferential direction. This signal can, for example, be derived from the activation signal of the deflecting coil 54. This signal is then at the same time information about how the fan-shaped x-ray light 62 is angularly oriented in the examination plane. The programmable processor 87 then has a subunit 90 which is supplied with the output signals of the detector strip 68 and stores these.

If the division of the detector elements 68(*i, j*) is markedly smaller than the division of the interference figure, the subunit 90 can directly match a sinusoidal intensity profile to the output signals of neighbouring detector elements, e.g. by least square fit or Fourier transformation. This intensity profile is compared with a reference intensity profile which had been obtained without an object and is stored in a reference profile memory 91. By comparison, the phase shift due to the object is then calculated.

The mean absorption value of the object and the amplitude of the sinusoid-like pixel information are available, as in other phase contrast methods, likewise as imaging information and can also be utilised in the further processing units.

The phase shifts for the different image pixels are then stored in a memory 92, in memory areas 92-1, 92-2, . . . 92-$i$, . . . corresponding to the layers of the object, in which the phase shifts calculated pixelwise represent an initially numeric image of the object.

By treating these numerical values similar to grey scale values of an ordinary image, it is then possible, using conventional tomographic reconstruction methods which may of course also be applied to partial volumes, and using conventional image processing methods, to produce tomography images which are visually improved with respect to contrast and which an observer then evaluates on a screen 94. Alternatively or additionally, the images are also output on a printer 96 and stored in a patient or object database memory 98.

If no detector strips 68 are present in which the division of the detector elements 68-$i$ is significantly (a factor of 4 and above) smaller than the division of the interference pattern, the determination of the phase position changed by the object is carried out successively by slightly changing test conditions which affect the formation of the interference patterns. Suitable changes are primarily changes in the position of the focal spot F of the electron beam 56, changes in the position of phase grating 64 and amplitude grating 66.

These changes must be small compared with the grating constant of the x-ray grating used. They are subdivided into a number of steps corresponding to the number of sampling points for the sine-like grey scale value signal, the path sum of the steps in total corresponding to the grating constant of the x-ray grating used. Such small changes are obtained by radial displacements of the focal spot F on the target 58 inclined as shallow as possible or by adjusting or tilting of an x-ray grating by a means for changing one or more relative positions. The means in one example can include microactuators 146, e.g. piezoelectric actuators, as indicated in FIG. 20 acting in a translatory manner on the phase x-ray grating 64.

It is understood that a plurality of the changes mentioned can also be in combination. Further, the means for changing one or more relative positions can include a linear drive, a rotary drive, or a tilting device. The means can include the aforementioned microactuator, such as a piezoactuator, i.e., a piezoelectric actuator, a magnetorestrivtive actuator, or an electret actuator.

The interference figure is then measured again for different positions of the movable components. The different output signals of the detector elements 68-*i* which are determined for different relative positions k are stored in memory fields of the memory 90.

For each pixel there are then a larger number of sampling points (analogue memory cells of the memory areas 90-*k*) which are used for determining an intensity sine curve. This is done in detail in a similar manner to that described above for the case of very finely divided detector strips. From this sine curve, the phase shift relative to the reference measurement without an object is then calculated again. If required, here too, in addition to the phase information, the mean grey scale value and the amplitude of the sinusoid-like profile can also be further utilised.

From the phase positions which have been measured for the different pixels with and without an object, the phase image of the object can then be created again.

It is understood that the reference interference image of the tomography device alone (without an object; reference image) is a device constant which only needs to be re-determined at longer intervals, in order to eliminate ageing effects and possibly also thermal instabilities. Of course, the reference interference pattern also has to be re-determined when the geometry of the arrangement changes for special examinations.

It can be seen that the above-described phase contrast tomography device has no components which are to be machined to high accuracy, except for the x-ray gratings and the detector strip. It is only necessary to move the object mechanically in the phase contrast tomography device if the imaging volume is to be greater than the grating structure comprising 20 layers.

It is thus suitable for use in the medical, dental and veterinary-medical fields also under non-laboratory conditions. The same applies to the use also in the fields of material testing and security systems (checking items of luggage etc.).

Figure 22:
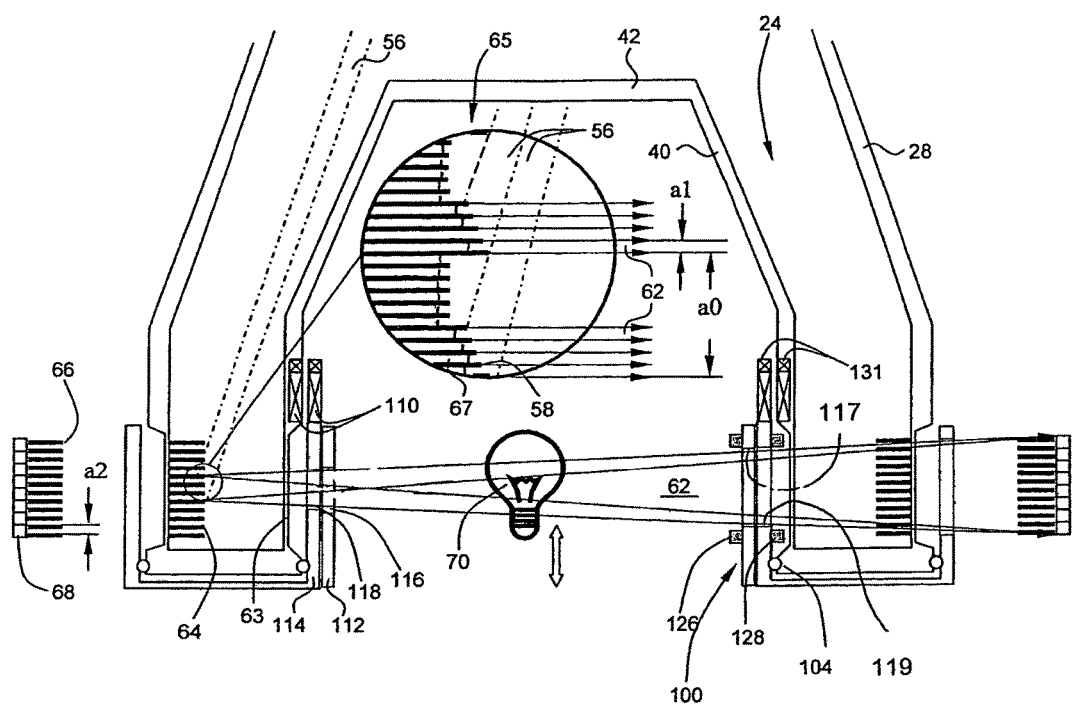
FIG. 22 shows an illustration of an x-ray tomography device which allows an exact radial irradiation and in which the target structure and the first x-ray-light diffraction structure are combined in one component, a rotating screen device being additionally provided.

FIG. 22 illustrates a modified tomography device, in which the x-ray diffraction structure 64 and the target ring 58 are combined into one component. The lamellae of the x-ray diffraction structure 64 are arranged at a grating spacing a1 and preferably consist, just as the target 58, of a material of high density and high atomic number, so that the surface of the diffraction structure is in principle well suited for generating x-rays.

Preferably, in such a combined unit 65 of the target and x-ray diffraction structure, interspaces between the grating lamellae are filled with a material 67 which is of good thermal conductivity and low radiation absorption, and which may at the same time have an x-ray filter effect.

The structuring required for the coherence of the source point is produced by the projecting groups of lamellae illustrated in the combined unit 65, which are arranged at a spacing a0. As a result of the projection of the lamellae in groups, the electron beam impinging obliquely from above is shaded in the intermediate regions, so that no more x-ray radiation is generated there. Owing to the illustrated sawtooth-roof-like inner boundary surface of the lamellae stack, the intensity of the electron beam 56 is better utilised. In this variant, the irradiation of the object can take place in an exact plane, in contrast to the variants according to FIGS. 2 to 6.

Figure 23:
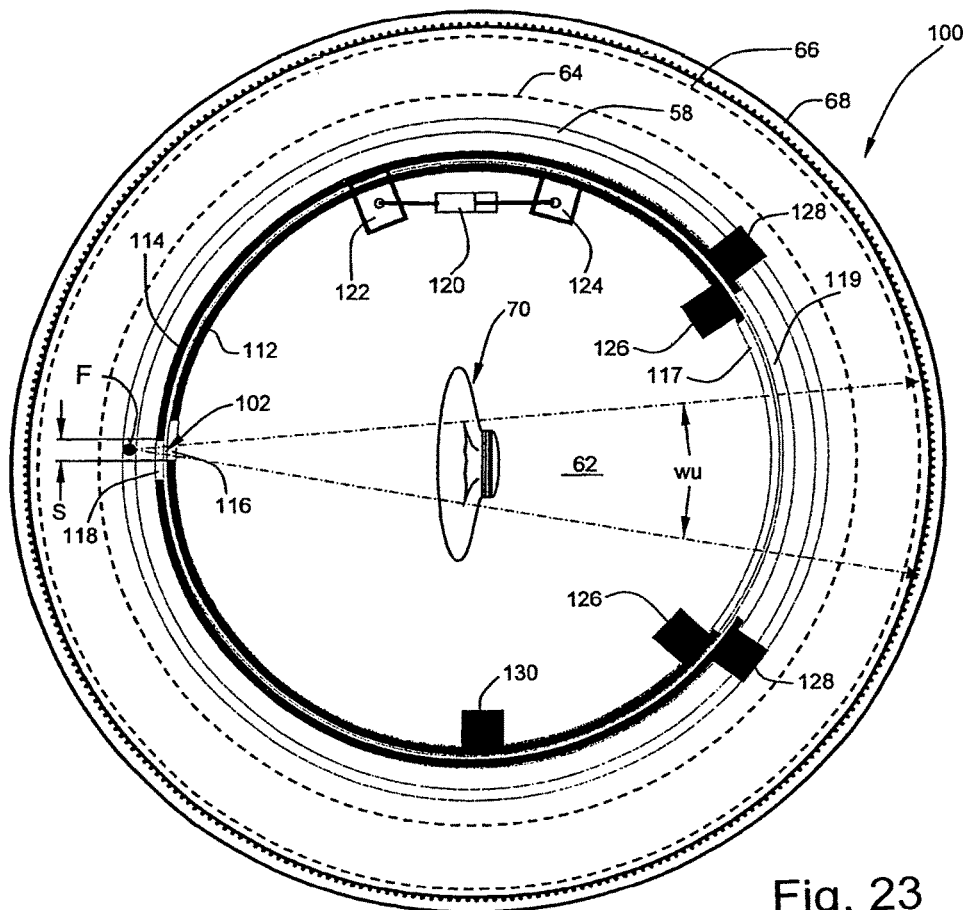
FIG. 23 shows a schematic view of a width-adjustable rotating screen for lateral limitation of an x-ray beam in an examination plane.

In addition, a rotating screen device denoted as a whole by 100 is illustrated in FIGS. 22 and 23, which device is not necessary for the functioning of the tomography device in the case of technical objects, but is useful for reducing the radiation exposure for patients in medical applications. It comprises components 100 to 131.

The x-ray beam fan 62 is limited to the required limit of the angle wu and we by x-ray windows 116, 118 adjustable relative to one another. A bearing 104 of the rotating screen is realised by a large-diameter ball bearing at the bottom 30 of the housing 24, but an air cushion bearing or a magnetic bearing would also be usable here.

A drive 110 and a position indication 131 ensure the desired dynamic positioning with respect to the x-ray emission point F.

The screen 102 consists of two cylindrical screen parts 112, 114 which, except for windows 116 to 119 transparent to x-ray light, are non-transparent to x-ray light.

The windows 116 and 118 thus together define a gap S, which is adjustable by rotation of one of the screen parts 112, 114 on the other, the x-ray beam fan, emerging in the direction of the object, in the circumferential direction. The screen parts 112, 114 can be adjusted, for example, by manual adjustment of an elongated-hole connection in the circumferential direction relative to one another, in order to change the width of the gap S.

Alternatively, the two screen parts 112, 114 can also be coupled via an actuator 120 acting in the circumferential direction, which acts on arms 122, 124 attached to the screen part 112 and 114, respectively.

Balancing bodies 126 and 128, which are arranged symmetrically in each case on both sides of the windows 116, 118, serve for mass balancing for the lighter windows 116, 118.

A further balancing body 130 is arranged, diametrically opposite the adjusting device 120, 122, 124, on the inner screen part 112 and balances out the unbalance produced by the adjusting device.

The actuator 120 is wirelessly supplied with energy and remotely controlled wirelessly (optionally via the same transmission route).

Figure 24:
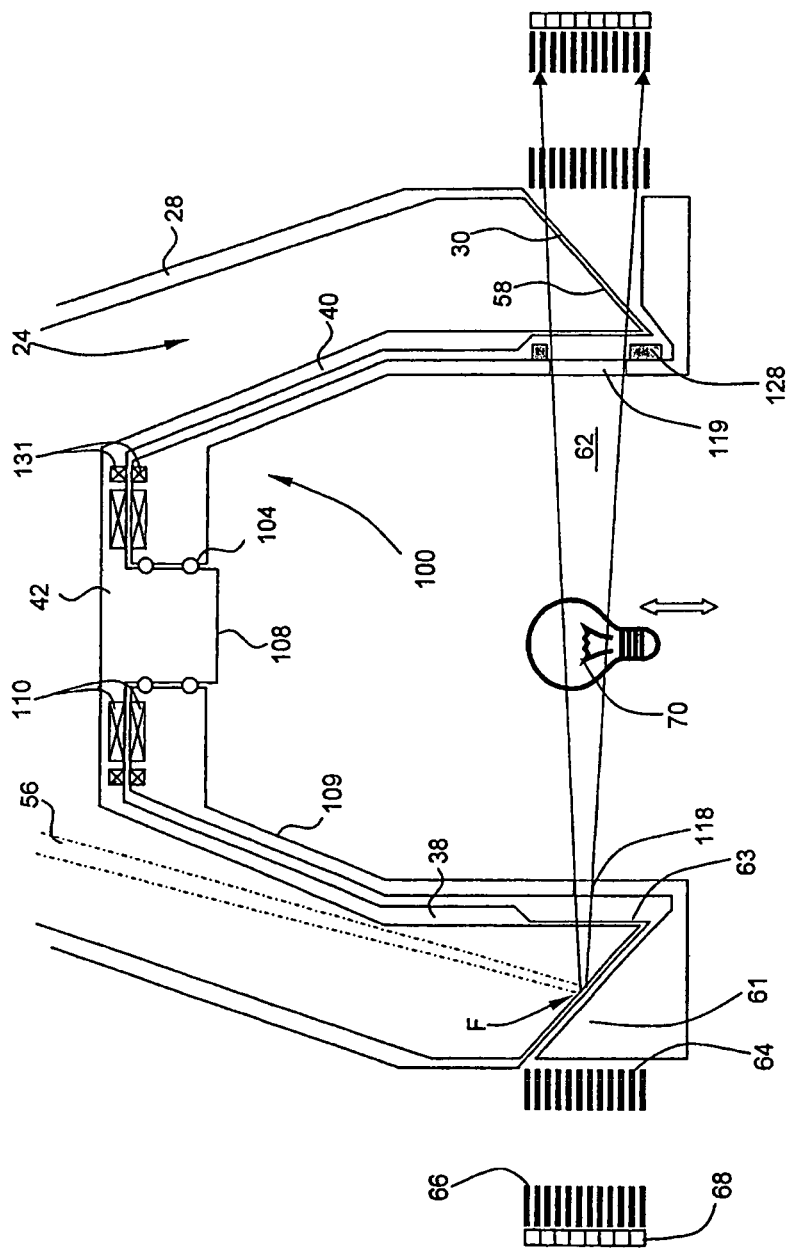
FIG. 24 shows an illustration of an x-ray tomography device with the x-ray beam passing through the outlet window twice and additionally passing through the target and the housing wall, thus likewise allowing an exact radial irradiation.

When using the above-described screen 102, the transverse dimension of the x-ray light 62 in the examination plane can be preset via the gap S. FIG. 24 illustrates a further variant, with which an irradiation of the object can likewise be carried out in an exact plane.

Here, the target ring 58 and the housing bottom 30 is dimensioned such that the x-ray fan can radiate through the latter on the opposite side.

FIG. 24 illustrates additionally a modification of the rotating screen with a suspension 109 in the form of a bell or spoked crown, the bearing 104 of which is fastened to a central axle 108 which is fastened to the end wall 42 of the housing 24. On the region of the rotating screen adjacent to the emission point F there is situated additionally a co-rotating shielding body 61 which limits the radiation emission into the detector regions adjacent to the emission point F.

The evaluation of the output signals of the detector row 68 is carried out using the screen bodies according to FIG. 22 to FIG. 24 such that in each case a partial region of the detector row 68 on which usable interference patterns are obtained is activated and its output signals are evaluated. The selection of this region is carried out using the position indicator 131 or by evaluation of the deflecting signals for the deflecting coil 54.

Figure 25:
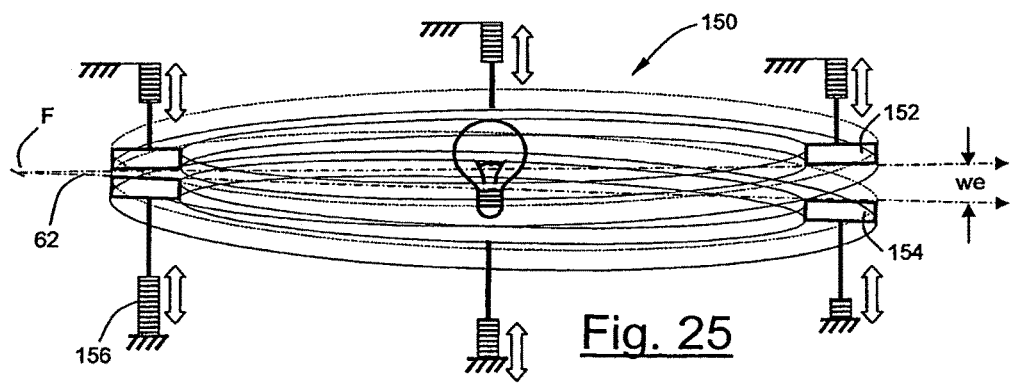
FIG. 25 shows an illustration of a screen which limits the rotating x-ray fan in its height through a wobbling motion and thus reduces the irradiation dose.

FIG. 25 shows a screen 150 which limits the spread angle of the x-ray fan in the elevation direction (spread angle in the axial sectional plane).

An upper screen ring 152 and a lower screen ring 154 are fastened to a suitable place of the housing 24 via in each case at least three actuators (lifting magnets, vibrating magnets, piezo-positioners, pneumatic cylinders, magnetostrictive actuators) 156, with optionally also one of the two screen rings 152, 154 being stationarily mountable. By a phase-shifted sinusoidal control of the actuators, the corresponding screen can now execute a wobbling motion, whereby the elevation angle we of the x-ray fan 62 is locally limited and at the same time it is ensured that the radiation in the x-ray fan 62 which penetrates the patient can also be registered on the detector. This makes it possible to reduce the radiation exposure for the patient.

Figure 26:
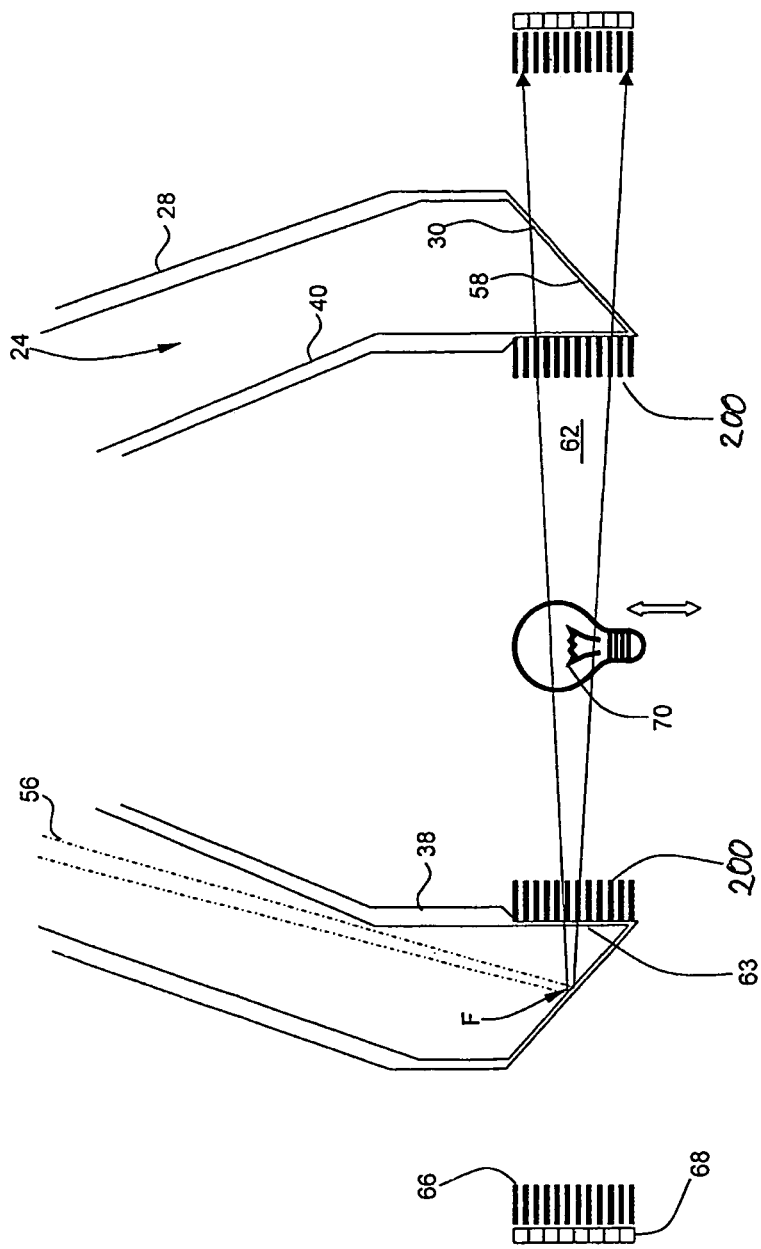
FIG. 26 shows an axial section through a phase contrast x-ray tomography device having a grating which surrounds the examination region and at the same time performs the function of a coherence grating and of a phase grating.

FIG. 26 shows a phase contrast x-ray tomography device according to a further exemplary embodiment of the invention.

In this phase contrast x-ray tomography device, the bottom wall 30 of the evacuated housing 24 on which the truncated-cone-shaped target 58 is arranged, and also the target 58 itself, are formed from a material transparent to the x-ray light. The opening angle of the truncated-cone-shaped target 58 is furthermore chosen such that the x-ray light, after it has emerged from the outlet window 63 and passed through the examination region, impinges on the outlet window 63 again on the diametrically opposite side.

Arranged radially inside when seen from the outlet window 63 is a grating 200 which surrounds the examination region and simultaneously performs the function of the coherence grating 12 and of the phase grating 64. Arranged radially outside the bottom wall 30 are the amplitude grating 66 and the detector strip 20, the functioning of which is unchanged compared with the previous exemplary embodiments.

Otherwise, the phase contrast x-ray tomography device functions as follows:

The x-ray light generated at the focal spot F on the target 58, after it has emerged from the outlet window 63, impinges firstly on the grating 200, whereby x-ray light is generated with sufficient coherence for the phase measurement.

After passing through the examination region, the x-ray light impinges on the grating 200 again and passes through the latter in the opposite direction. The grating 200 serves now, as part of the phase measuring device together with the amplitude grating 66 and the detector strip 20, to detect the phase position of the x-ray light. The x-ray light enters the housing 24 again via the outlet window 63, in order thereupon to pass through the target 58 and the bottom wall 30. There, it finally impinges on the amplitude grating 66 and the detector strip 20.

The exemplary embodiment just described thus makes it possible with only two gratings to realise a phase contrast tomography device which does not require any parts moving around the object to be examined in order to detect the individual tomography projections. If a detector strip 20 with a sufficiently high resolution (for example with the resolution of the amplitude grating 66) were used, the amplitude grating 66 could moreover be dispensed with.

In combination with the exemplary embodiment according to FIG. 22, a phase contrast x-ray tomography device would even be conceivable, in which only a target provided with a grating structure and a high-resolution detector are used.

The invention claimed is:

1. A phase contrast x-ray tomography device comprising:
    a vacuum vessel;
    a target;
    an x-ray light source, which has at least one electron beam deflectable in the vacuum vessel and moving on a present path over the target at least partially surrounding an examination region in order to generate on the target at least one focal spot emitting x-ray light,
    an x-ray-light detection unit, which comprises a stationary x-ray light phase measuring device over which the x-ray light is swept upon movement of the x-ray light, and
    an evaluating device, which is supplied with output signals of the stationary x-ray light phase measuring device and is designed to calculate from the output signals an object image obtained by phase contrast.

2. A phase-contrast x-ray tomography device according to claim 1, wherein the x-ray light source is configured so that the at least one electron beam can be modulated in its intensity.

3. A phase contrast x-ray tomography device according to claim 2, wherein the x-ray light source is configured so that the at least one electron beam can be switched on and off path-dependently.

4. A phase contrast x-ray tomography device according to claim 1, wherein the x-ray light source is configured so that the at least one electron beam can be moved intermittently by equal increments.

5. A phase contrast x-ray tomography device according to claim 1, wherein the x-ray light source comprises an electron beam source, wherein the target is at least partially rotationally symmetrical, truncated cone shape, or a part of such, which is widened in a direction towards the electron beam source of the x-ray light source and has an opening angle such that the image of the focal spot is adapted to a Talbot interferometer of the stationary x-ray light phase measuring device.

6. A phase contrast x-ray tomography device according to claim 1, wherein the phase contrast x-ray tomography device comprises a housing wall, wherein the x-ray light source comprises an electron beam source, wherein the target comprises a radially outer edge or a radially inner edge that carries a filter wall, which runs back substantially axially in a direction of the electron beam source and is carried by the target or the housing wall carrying the target, the target greatly absorbing or blocking x-ray radiation.

7. A phase contrast x-ray tomography device according to claim 1, wherein the stationary x-ray light phase measuring device comprises a Talbot interferometer, wherein the x-ray light source comprises an electron beam source, wherein the target of the x-ray light source has a basic body made from a basic material with a low atomic number and high thermal conductivity, and in that the target has a functional layer, facing the electron beam source, which is produced from a material with a high atomic number, which has good thermal conductivity and/or is adapted to the Talbot interferometer.

8. A phase contrast x-ray tomography device according to claim 1, wherein the stationary x-ray light phase measuring device comprises a Talbot interferometer, wherein the x-ray light source comprises an electron beam source, wherein the target comprises a functional layer, facing the electron beam source, which is produced from a material allowing the generation of x-ray light, the spectrum of which has a peak at a wavelength which is adapted to the Talbot interferometer.

9. A phase contrast x-ray tomography device according to claim 1, wherein the stationary x-ray light phase measuring device comprises a detector configured as a closed ring, which is circular or polygonal.

10. A phase contrast x-ray tomography device according to claim 1, wherein the stationary x-ray light phase measuring device comprises a detector, which comprises an arrangement of detector elements with a plurality of rows, wherein a row height of the plurality of rows is a fraction of a pixel resolution.

11. A phase contrast x-ray tomography device according to claim 1, further comprising an x-ray grating, wherein, seen in the beam direction behind the x-ray light source, the x-ray grating is arranged as a coherence grating.

12. A phase contrast x-ray tomography device according to claim 11, wherein the x-ray grating at least partially surrounds the examination region, the x-ray grating, seen in the beam direction of the x-ray light in front of the examination region, acting as a coherence grating and, seen in the beam direction of the x-ray light behind the examination region, acting as an x-ray diffraction structure of the stationary x-ray light phase measuring device.

13. A phase contrast x-ray tomography device according to claim 1, wherein the stationary x-ray light phase measuring device comprises an interference device and a detector, the interference device having at least one x-ray-light diffraction structure which, seen in the beam direction, is arranged in front of the detector of the stationary x-ray light phase measuring device.

14. A phase contrast x-ray tomography device according to claim 13, wherein the at least one x-ray-light diffraction structure comprises two x-ray-light diffraction structures, which are x-ray gratings, spaced in the beam direction, which are arranged spaced at Talbot spacing in the beam direction.

15. A phase contrast x-ray tomography device according to claim 13, wherein the interference device is adapted to the center of gravity or a desired spectral region of the spectrum of the x-ray light source.

16. A phase contrast x-ray tomography device according to claim 13, wherein the interference device is configured simultaneously as a filter for long-wave regions of the spectrum of the x-ray light source.

17. A phase contrast x-ray tomography device according to claim 13, wherein the at least one x-ray-light diffraction structure is configured as a ring or ring segment and has a circular or polygonal basic geometry.

18. A phase contrast x-ray tomography device according to claim 17, wherein the at least one x-ray light diffraction structure lies nearest an object, on its side facing the object, and is a superposed double-periodic diffraction structure with a first grating constant, which satisfies a Talbot condition for this diffraction structure, and with a second periodic spacing constant, which satisfies the Talbot condition for the coherence of the source point, and is formed by shading regions with respect to the at least one electron beam.

19. A phase contrast x-ray tomography device according to claim 17, wherein the phase contrast x-ray tomography device comprises a filter wall, and wherein the x-ray light that penetrates an object runs substantially radially and undergoes a further filtering of the energy spectrum owing to the penetrated regions of the filter wall and owing to the materials, penetrated again, of a section of the target lying on the opposite side.

20. A phase contrast x-ray tomography device according to claim 13, wherein the at least one x-ray-light diffraction structure is periodic in the direction of a device axis.

21. A phase contrast x-ray tomography device according to claim 13, wherein the at least one x-ray-light diffraction structure is periodic in the circumferential direction.

22. A phase contrast x-ray tomography device according to claim 1, further comprising a coherence grating and means for changing one or more relative positions between one or more of the following components or parts thereof, on one hand, and another of the following components or parts thereof, on another hand: the x-ray light source, the coherence grating; and the stationary x-ray light phase measuring device.

23. A phase contrast x-ray tomography device according to claim 22, wherein the means for changing one or more relative positions comprise a microactuator.

24. A phase contrast x-ray tomography device according to claim 22, wherein the stationary x-ray light phase measuring device comprises an x-ray-light diffraction structure, wherein the means for changing one or more relative positions is configured to change a diffraction geometry of the x-ray-light diffraction structure of the x ray light phase measuring device.

25. A phase contrast x-ray tomography device according to claim 1, wherein a region of the vacuum vessel adjacent to a path plane of the x-ray light is at least partially transparent to x-ray light and the stationary x-ray light phase measuring device is at least partially or wholly arranged radially outside the vacuum vessel.

26. A phase contrast x-ray tomography device according to claim 1, wherein the x-ray light source has an outlet gap for the x-ray light, which runs in a plane laying perpendicular to a device axis and is bounded by an at least partially circular or polygonal screen and presents an elevation spread angle for the x-ray light, wherein the elevation spread angle is adapted to a corresponding detector dimension, and/or a circumferential spread angle adapted in such a manner.

27. A phase contrast x-ray tomography device according to claim 26, further comprising a further screen acting in the circumferential direction, and which rotates about the device axis synchronously with respect to the x-ray light and presents x-ray light with a small circumferential spread angle in the circumferential direction.

28. A phase contrast x-ray tomography device according to claim 26, wherein the phase contrast x-ray tomography device comprises a filter wall, wherein the outlet gap and the position of the focal spot of the at least one electron beam of the x-ray light source are offset axially relative to one another, the outlet gap being combined with the filter wall and further being configured as a vacuum window.

29. A phase contrast x-ray tomography device according to claim 1, further comprising a plurality of screen windows that follow one another in the circumferential direction.

30. A phase contrast x-ray tomography device according to claim 29, wherein the plurality of screen windows is formed by screen bodies that following one another equidistantly in a circumferential configuration, wherein the screen bodies are of a bar-shaped configuration.

31. A phase contrast x-ray tomography device according to claim 29, wherein the at least one electron beam is moved intermittently by equal increments, and wherein the increments are adapted to the spacing of the plurality of screen windows.

32. A phase contrast x-ray tomography device according to claim 31, wherein the division of the path of the at least one electron beam is phase-shifted by one phase shift relative to the division of the plurality of screen windows.

33. A phase contrast x-ray tomography device according to claim 32, wherein the phase shift is chosen path-dependently so that a present partial region of an object is irradiated.

* * * * *

UNITED STATES PATENT AND TRADEMARK OFFICE
CERTIFICATE OF CORRECTION

PATENT NO. : 10,076,297 B2
APPLICATION NO. : 14/387786
DATED : September 18, 2018
INVENTOR(S) : Walter Bauer Page 1 of 1

It is certified that error appears in the above-identified patent and that said Letters Patent is hereby corrected as shown below:

In the Claims

Column 20, Lines 36-37, Please delete "of the x ray light phase measuring device".

Signed and Sealed this
Eleventh Day of December, 2018

Andrei Iancu
*Director of the United States Patent and Trademark Office*